US008750615B2

(12) United States Patent
Rollins et al.

(10) Patent No.: US 8,750,615 B2
(45) Date of Patent: Jun. 10, 2014

(54) SEGMENTATION AND QUANTIFICATION FOR INTRAVASCULAR OPTICAL COHERENCE TOMOGRAPHY IMAGES

(75) Inventors: Andrew Rollins, Highland Hts., OH (US); David Wilson, Clev. Hts., OH (US); Marco Costa, Pepper Pike, OH (US); Hiram Bezerra, Shaker Heights, OH (US); Zhao Wang, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 131 days.

(21) Appl. No.: 13/196,845

(22) Filed: Aug. 2, 2011

(65) Prior Publication Data

US 2012/0075638 A1 Mar. 29, 2012

Related U.S. Application Data

(60) Provisional application No. 61/369,883, filed on Aug. 2, 2010.

(51) Int. Cl.
*G06K 9/34* (2006.01)
*G06K 9/00* (2006.01)

(52) U.S. Cl.
USPC ............................ 382/173; 382/131; 382/180

(58) Field of Classification Search
USPC .................. 382/131, 132, 159, 160, 224–228
See application file for complete search history.

(56) References Cited

U.S. PATENT DOCUMENTS

| 6,941,016 B1* | 9/2005 | Wagman et al. ............... 382/199 |
| 2008/0091105 A1* | 4/2008 | Weinbaum et al. ........... 600/443 |
| 2009/0306520 A1* | 12/2009 | Schmitt et al. ................ 600/476 |
| 2010/0278405 A1* | 11/2010 | Kakadiaris et al. ........... 382/131 |
| 2010/0278735 A1* | 11/2010 | Waxman et al. ............... 424/9.1 |
| 2012/0213423 A1* | 8/2012 | Xu et al. ....................... 382/131 |

OTHER PUBLICATIONS

Sihan et al., "Fully automatic three-dimensional quantitative analysis of intracoronary optical coherence tomography", Catheterization and Cardiovascular Intervecntions 74:1058-1065, 2009.*
Bazant-Hegemark et al., "Towards automated classification of clinical optical coherence tomography data of dense tissues", Lasers Med Sci (2009) 24:627-638, published Oct. 2008.*
Chau et al., Mechanical analysis of atherosclerotic plaques based on optical coherence tomography, Annals of Biomedical Engineering, vol. 32, No. 11, Nov. 2004.*
Pauly et al., "Semi-automatic matching of OCT and IVUS images for image fusion", Proc. of SPIE vol. 6914N, 2008.*
Singh, K.C., et al., "Comparative Study on Thresholding", International Journal of Instrumentation, Control & Automation (IJICA), vol. 1, Issue 1, 2011 pp. 73-77.

* cited by examiner

*Primary Examiner* — Vu Le
*Assistant Examiner* — Soo Park
(74) *Attorney, Agent, or Firm* — Benesch Friedlander Coplan & Aronoff LLP

(57) ABSTRACT

A system and related methods for automatic or semi-automatic segmentation and quantification of blood vessel structure and physiology, including segmentation and quantification of lumen, guide wire, vessel wall, calcified plaques, fibrous caps, macrophages, metallic and bioresorbable stents are described, and including visualization of results. Calcified plaque segmentation can be used to estimate the distribution of superficial calcification and inform strategies stenting. Volumetric segmentation and quantification of fibrous caps can provide more comprehensive information of the mechanisms behind plaque rupture. Quantification of macrophages can aid diagnosis and prediction of unstable plaque and associated acute coronary events. Automated detection and quantification of metallic and bioresorbable stents can greatly reduce the analysis time and facilitate timely decision making for intervention procedures.

15 Claims, 27 Drawing Sheets

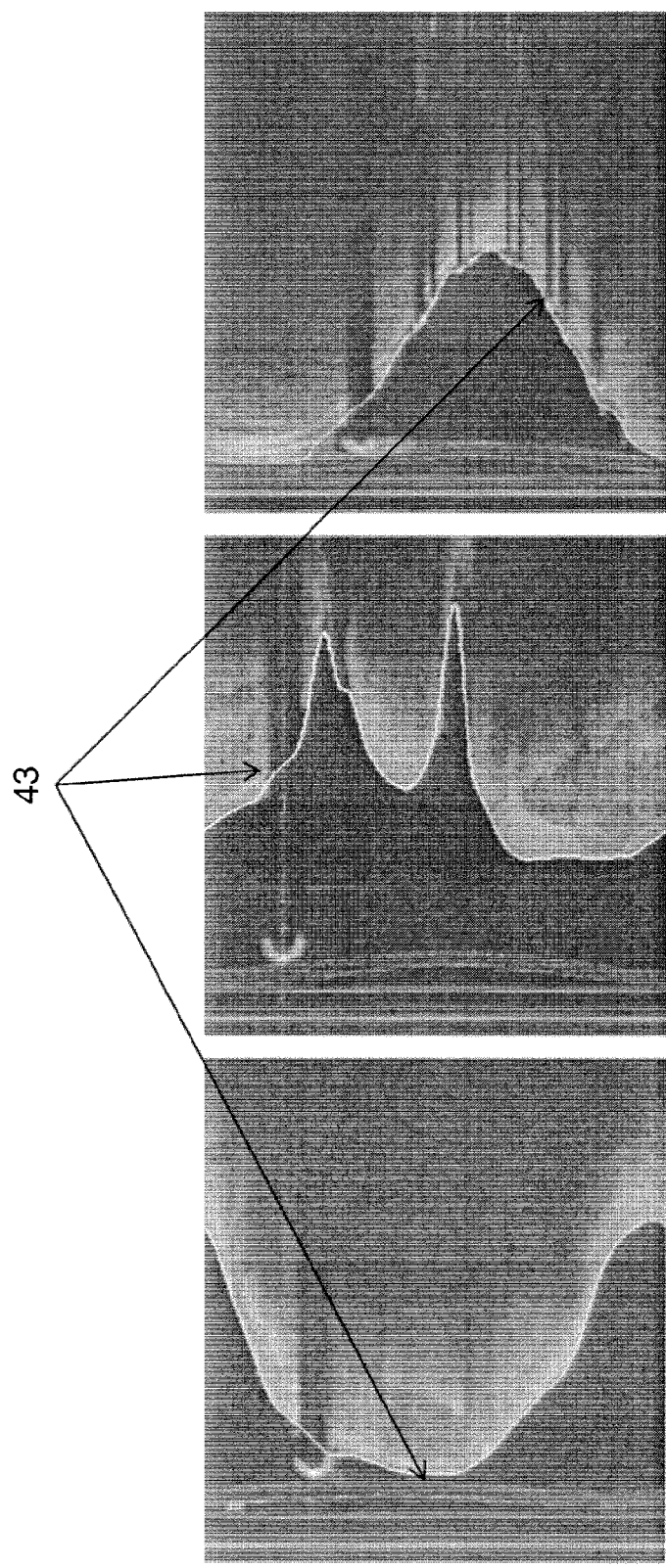

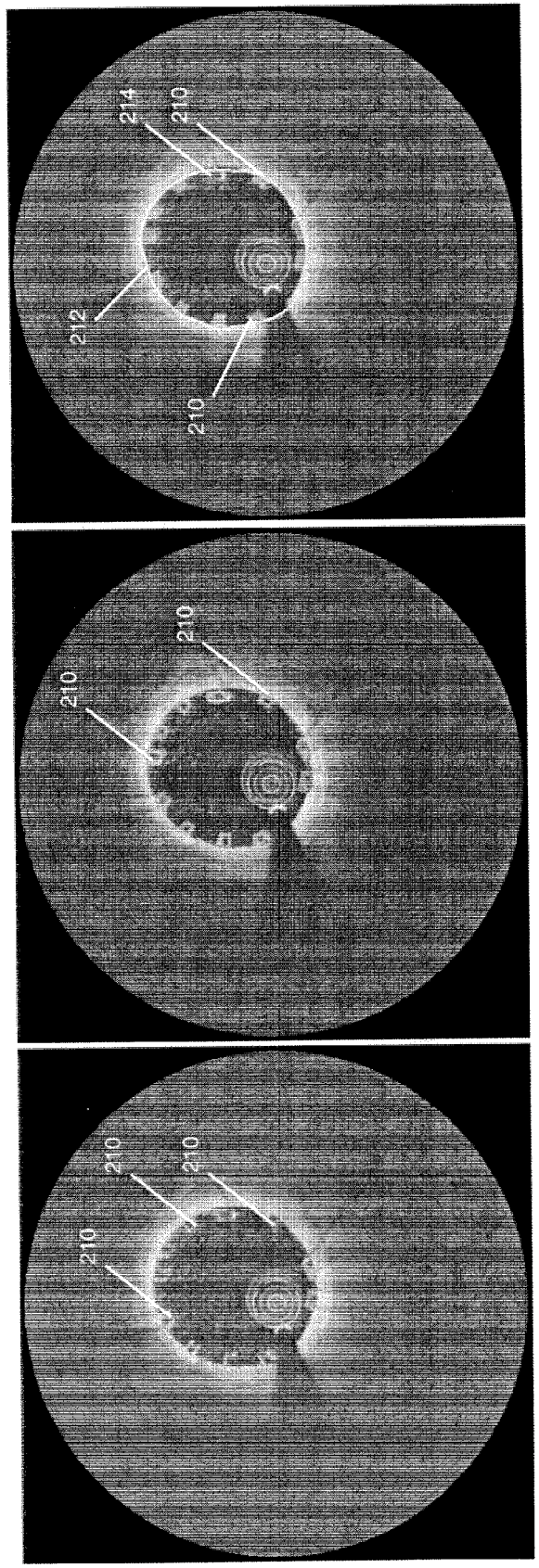

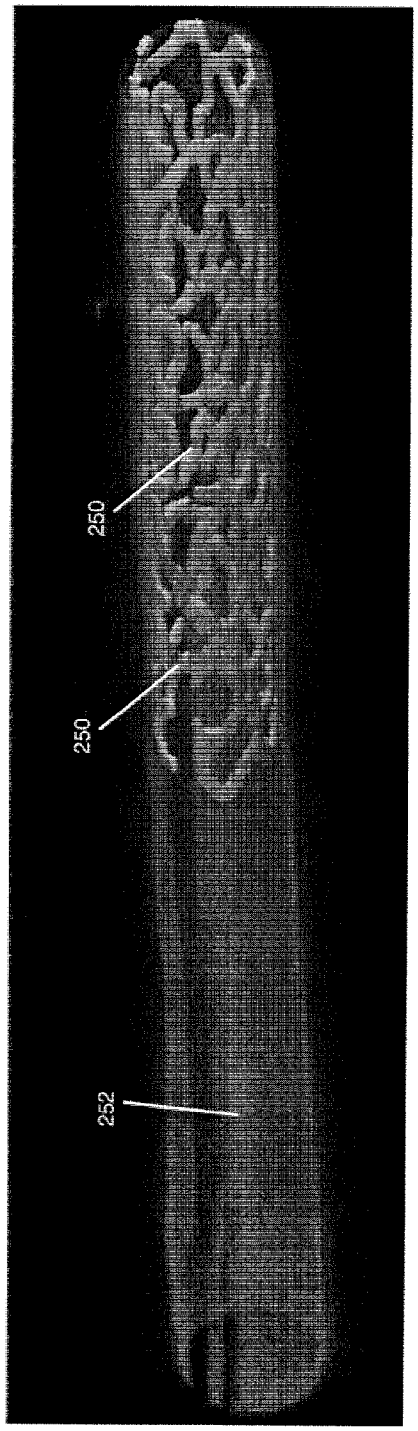
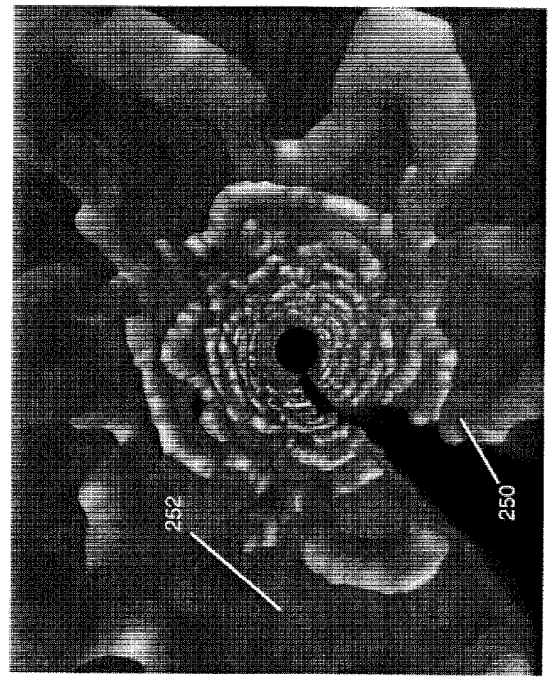
Figure 25A
Figure 25B

SEGMENTATION AND QUANTIFICATION FOR INTRAVASCULAR OPTICAL COHERENCE TOMOGRAPHY IMAGES

PRIORITY

This application claims priority to U.S. Provisional Patent Application No. 61/369,883 filed Aug. 2, 2010, which is incorporated herein by reference in its entirety.

FIELD OF THE INVENTION

The present disclosure relates to methods and apparatus for automatic and semi-automatic image analysis and presentation of blood vessel structure and pathophysiology using optical coherence tomography imaging. Image analysis includes classification and/or segmentation of structures such as the lumen, guide wire, vessel wall, calcified plaques, lipid, fibrous caps, macrophages, metallic and bioresorbable stents. Presentation of results includes various two dimensional (2D) and three dimensional (3D) visualizations of image analysis results.

BACKGROUND

Detection and quantification of various aspects of the physiology and structure associated with blood vessels can greatly improve diagnosis and treatment of patients. For example, investigation, diagnosis, staging, and treatment of atherosclerotic disease can be greatly facilitated by detection and quantification of types of plaque and macrophages, an indicator of inflammation. In addition, quantification of calcified lesions, such as their locations and volumes, can provide valuable information, for example, for optimal placement of coronary stents. Further, detection and quantification of structures such as stents can help evaluate risks of the malaposition and uncovered struts associated with thrombosis.

Intravascular Optical Coherence Tomography (OCT) has a resolution of better than 15 microns and is capable of visualizing the cross sectional morphology of blood vessels in detail, including any atherosclerotic plaques. However, many hundreds of images are created and analysis of image data can be a tedious and time-consuming process when done manually. Providing an automatic or semi-automatic system and method for segmentation and quantification of blood vessel structure and physiology, such as any lumen, calcified plaques fibrous caps, macrophages and stents that are present, is therefore beneficial.

BRIEF DESCRIPTION OF THE DRAWINGS

FIGS. 5A, 5B and 5C illustrate OCT images showing lumen segmentation results using a dynamic programming method.

FIG. 21A-C illustrates automatically detected bioresolvable stent struts, automatically determined malaposed struts and stent scaffold.

FIGS. 25A and 25B illustrate 3D view and fly-through view of BVS stents inside a vessel.

DETAILED DESCRIPTION

Figure 1:
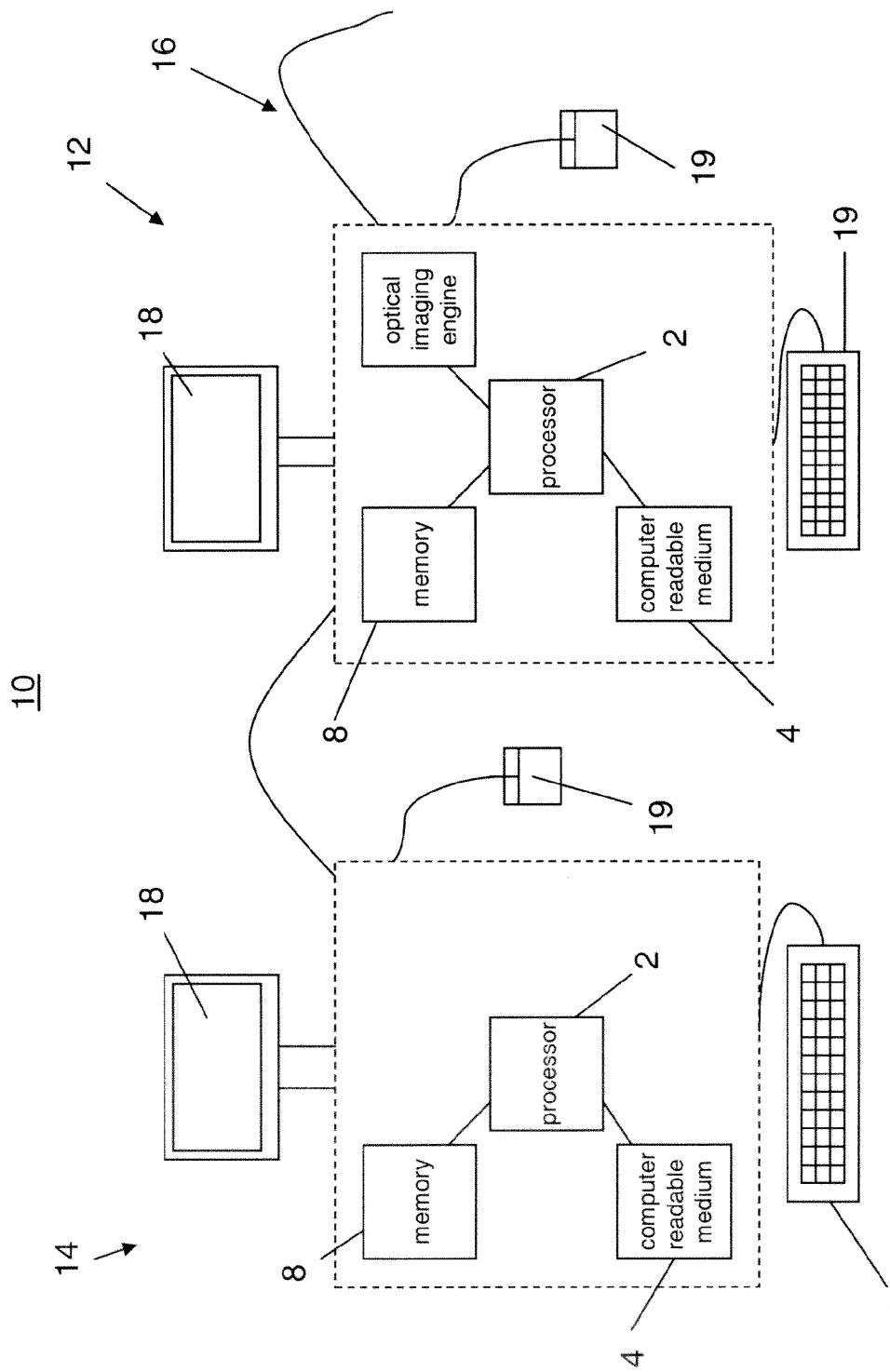
FIG. 1 illustrates an OCT imaging system that may be used to perform automatic segmentation and quantification of intravascular OCT images.

As shown in FIG. 1, an example OCT imaging system 10 includes an imaging station 12 that includes an input device 19, a catheter 16, which includes an optical fiber (not shown) that may be enclosed in a hollow tube or sheath (not shown), and a guide wire (not shown) for positioning the catheter. The imaging station may also include a processor 2, a computer readable medium 4 and memory 6. The imaging station may also include an optical imaging engine 8 used to generate the light source and acquire the reflected signal from the target, and which may also comprise a computer readable medium and processor. The imaging station 12 may process the received signal and reconstruct the image for presentation on a display 18. Instruments other than the catheter 16 may be used in emitting and receiving signals for OCT imaging, and the system and methods disclosed herein are not limited to use with the example instruments disclosed herein for emitting and receiving such signals.

The OCT imaging system 10 may also include a workstation 14 connected to the imaging station 12. The connection may be direct, as shown in FIG. 1, or may be connected through a network, such as through the internet or a local network. The workstation 14 may be a general purpose computer having computer readable media 4 and processor 2 configured to process and display images obtained by the imaging system 10. The principles and operation of OCT devices is known to those with skill in the art and will not be described in detail here. It will be appreciated that the system and method disclosed herein is applicable to all types of OCT, including but not limited to Fourier domain OCT (FDOCT) (also called Spectral Domain OCT (SDOCT), or Optical Frequency Domain Imaging (OFDI)) and Time Domain OCT (TDOCT).

Figure 2:
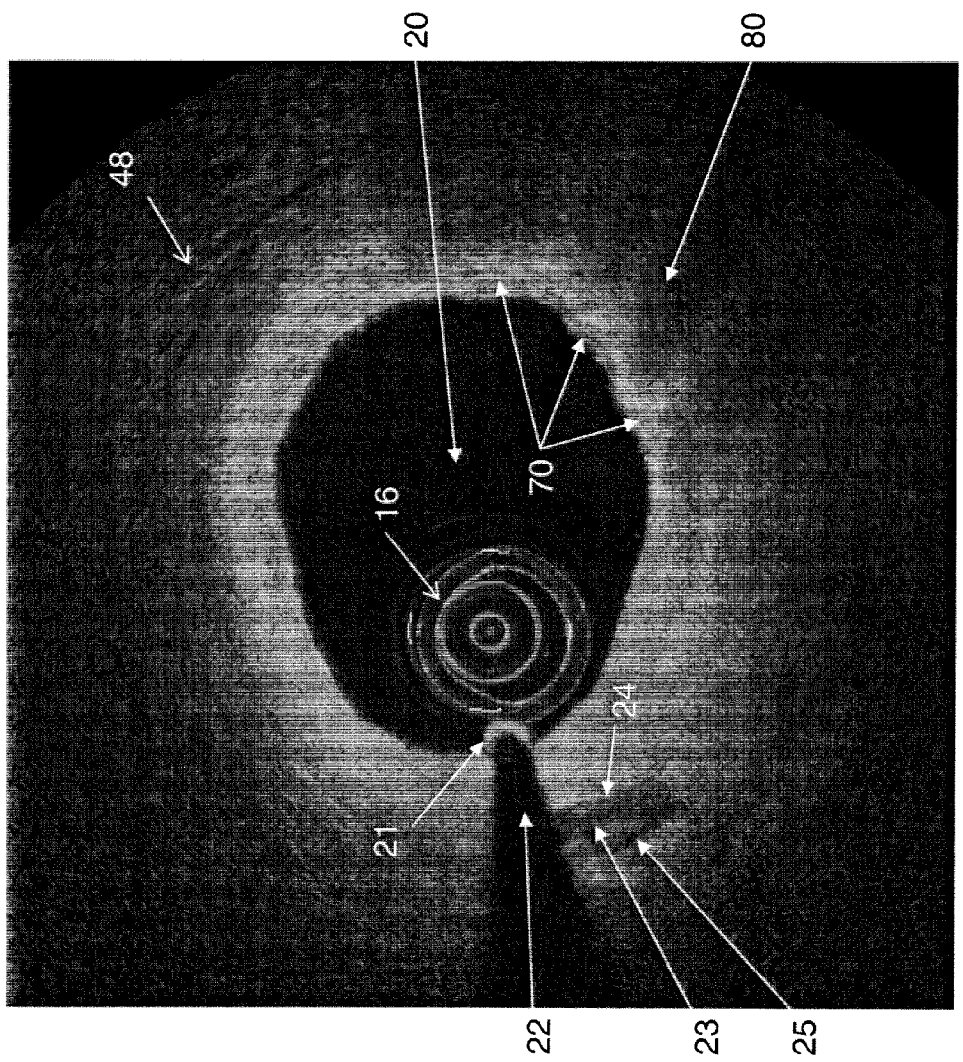
FIG. 2 illustrates an OCT image of a coronary artery having plaques, macrophages and adventitia tissues.

FIG. 2 shows a coronary artery OCT image. Typical features included in an OCT image are catheter 16, lumen 20, and guide wire 21. The artery shown in FIG. 2 also exhibits calcified arterial plaques or lesions 23, and macrophages 70. As can be seen in FIG. 2, the calcified plaques 23 may be characterized by two features: a sharp boundary and a low intensity core compared to surrounding tissue. The guide wire creates a bright artifact 21 corresponding to the front edge of the guide wire and a long shadow 22 from the center outward. Macrophages 70 are bright spots found within the fibrous cap of a lipid plaque 80. Depending on the presence of plaques and thickening of intima, adventitia tissues (majority fat) 48 sometimes can be seen in the image.

Figure 3:
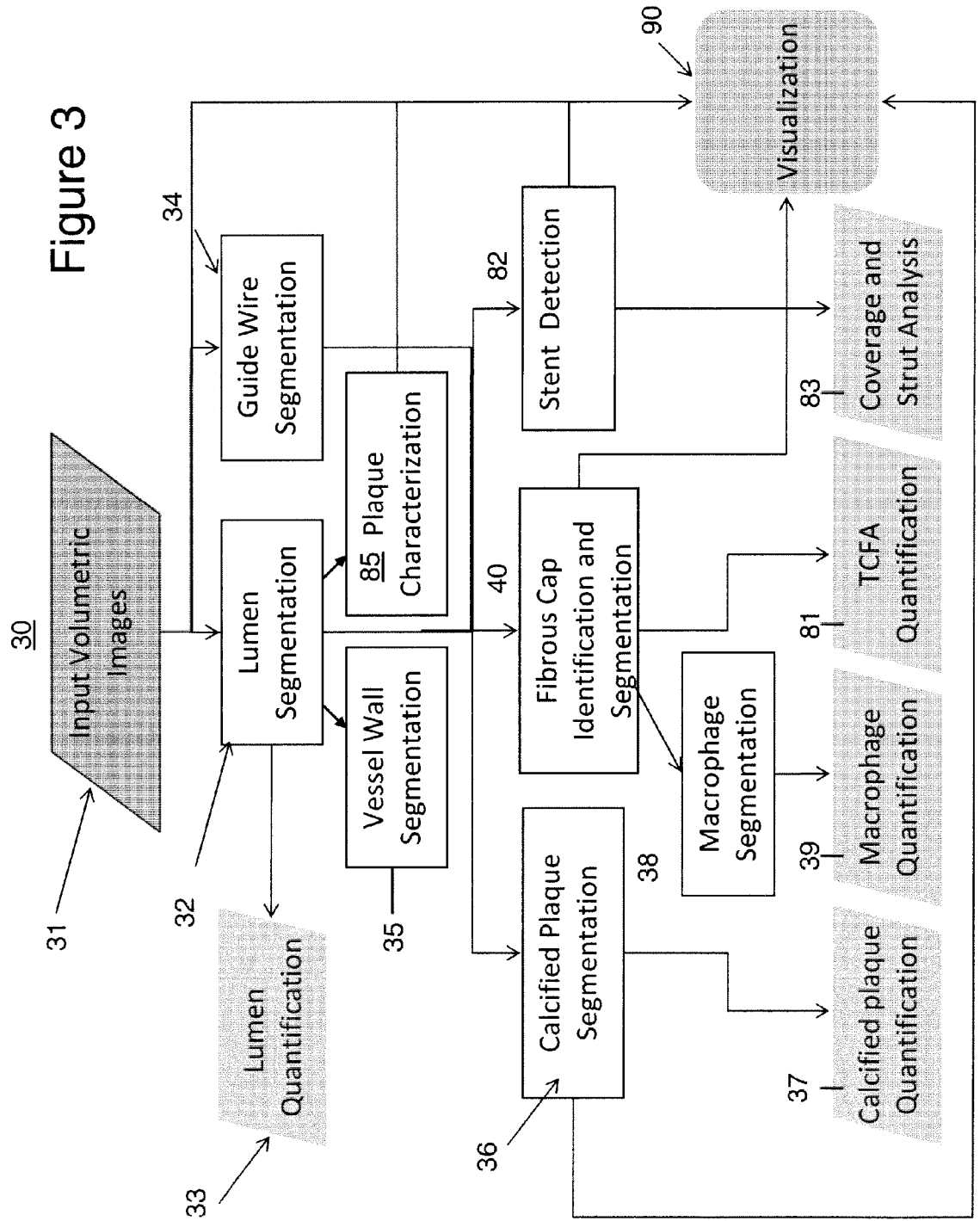
FIG. 3 illustrates an example method involving segmentation and quantification modules.

FIG. 3 illustrates an example of method 30 showing the relationships among different image processing modules for segmenting and quantifying blood vessel structure and physiology. In general, segmentation modules serve as the basis for quantification modules. After the input of volumetric image information 31, lumen segmentation 32 and guide wire segmentation 34, which may occur in parallel, serve as prerequisites for other modules of method 30. Lumen segmentation step 32 serves a basis for lumen quantification step 33. Vessel wall segmentation 35 provides regions of interest for a calcified plaque segmentation step 36, macrophage segmentation step 38 and characterization or classification of other types of plaque step. Calcified plaque quantification 37 may be performed once the calcified plaque segmentation step 36 has been performed. Likewise, macrophage quantification 39 may be performed once macrophage quantification 39 has been performed. Thin cap fibroatheroma (TCFA) quantification 81 is based on fibrous cap segmentation, for example performed in step 40. All segmentation, quantification and characterization results can be displayed in variety of different ways in step 90 in order to facilitate clinical diagnosis of atherosclerosis.

The method 30 may be applied in some instances to a rectangular representation of a coronary artery OCT image as shown in FIG. 2. In this approach, each horizontal row corresponds to a single "A-line" or "A-scan" of the OCT signal along the light propagation direction from the left lumen side to the right arterial wall. In other instances, the method 30 is applied to the polar representation of the coronary artery OCT image. The method 30 may be applied to the entire volumetric image set 31 obtained along a segment of a coronary artery. Further, in addition to segmentation and quantification using two-dimensional ("2D") image data, the methods and apparatuses described herein may be used with three-dimensional ("3D") image data. The method 30 may, for example, be implemented in a computer program comprising a series of instructions stored on a computer-readable medium located on an imaging station 12 or workstation 14 as described above, or any other manner of general purpose computer. In addition, any steps in method 30 described as automatic may be supplemented or substituted with manual intervention of a user.

Lumen Segmentation

Segmentation of the blood vessel lumen may serve as an early step for segmentation of a variety of structures and physiological aspects of blood vessels. Such structures and physiological features may include, but are not limited to, the layers of the vessel itself (e.g. intima, media and adventitia), calcified plaques, macrophages, or implants placed on or within the lumen (e.g., stents). For example, lumen segmentation is useful for estimating the coronary artery stenosis and guiding stent implantation.

The lumen segmentation step 32 may take as its input image the rectangular representation of the intravascular OCT image. In one embodiment, the lumen segmentation step 32 applies Otsu's method to generate a binary image of foreground and background pixels. The foreground pixels contain pixels corresponding to most of the superficial coronary wall, and may also contain pixels associated with the front edge guide wire artifact 21 and the catheter sheath 16. The pixels associated with the guide wire front edge artifact and the catheter sheath may be removed by applying an area constraint such that any isolated region with an area smaller than a certain threshold is removed. In one implementation, the threshold is $0.016MN$, where M and N are the number of rows and columns of the input image, respectively. Morphological closing is used to fill-in holes inside the foreground. Morphological opening is used to separate arterial wall from catheter if they are in contact with each other. In addition, the known size of the catheter may be used as input information to assist in identification and separation of the portions of the image resulting from the catheter from those resulting from the lumen.

Figure 4B:
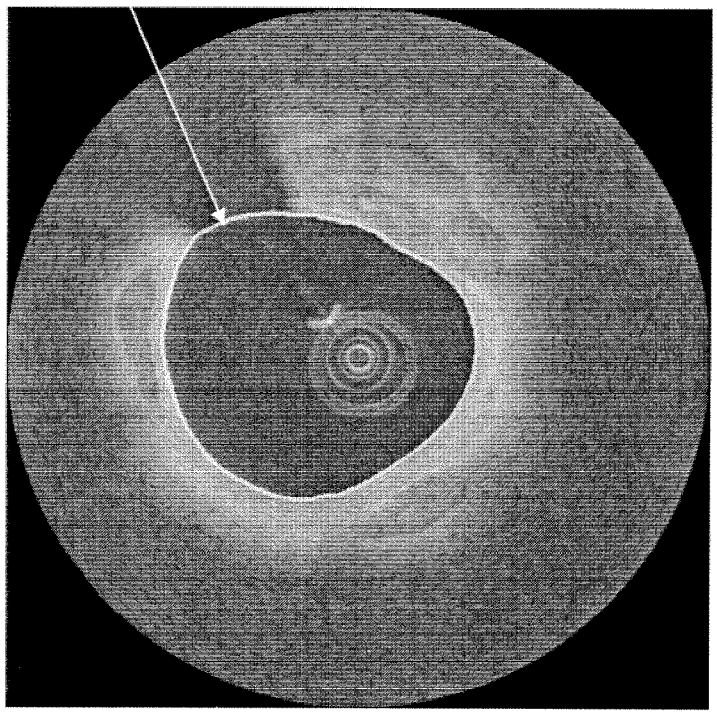
FIGS. 4A and 4B illustrate a foreground image resulting from applying lumen segmentation using Otsu's automatic thresholding method, and an OCT image showing a lumen border obtained from foreground pixels in FIG. 4A, respectively.
Figure 4A:
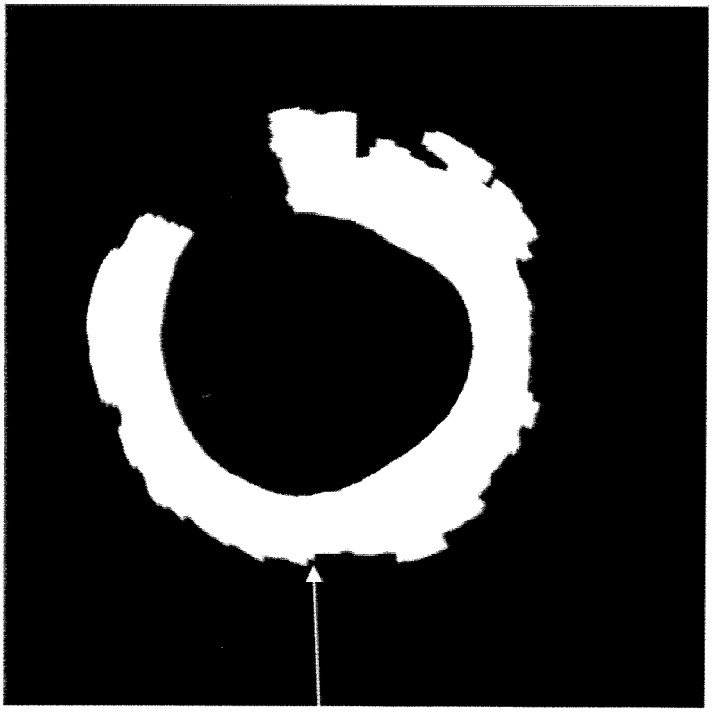

FIG. 4A illustrates the resulting foreground image corresponding to the bright superficial layer or "BSL" 41 of the coronary wall. As shown in FIG. 4B, the lumen border 42 is then identified by searching the first BSL pixel in the light propagation direction, for example from left to right in the rectangular view image along each A-scan. One or more sections of the border may be hidden by, for example, the guide wire shadow 22. The missing sections of the lumen border are connected by interpolation (e.g., linear, cubic or spline), as shown in FIG. 4B. It will be noted that in the rectangular coordinate representation of the intravascular OCT image, the last row of pixels at the bottom of the image represents a portion of the artery immediately adjacent the portion of the artery represented by the row of pixels at the top of the image of the next frame.

In another embodiment, the lumen segmentation is performed using a dynamic programming scheme by searching the contour that maximizes the difference between the sum of gray values outside and inside the boundary. Compared to other methods, dynamic programming guarantees a global optimum boundary. The method can be applied to a variety of cases including stented or non-stented arteries, and arteries with side branches. By defining an energy function $e(i, j)$ representing the intensity differences of the left and right side of the gray value at row i and column j, we have the following recursive function:

$$d[i, j] = \max_{j-n<j^*<j+n} \{d[i-1, j^*] + e(i, j)\}$$

Where d[i, j] is the accumulated energy representing the optimum boundary from the top row to row i and column j, j* is adjacent to j and n specifies connectivity. After recursively calculating the accumulated energy at every position, we explore all the possible paths from top to the bottom so the final solution is a global optimum. The position at the last row with the maximum accumulated energy is chosen and the optimum boundary is obtained by backtracking the path.

Methods described above are for 2D images. It is understood that 3D extensions of such methods exist. Potential advantages of a 3D method are additional robustness to gross segmentation errors, avoidance of small errors due to a lack of image evidence or artifact in one frame, and/or creation of a smooth lumen surface in 3D along the vessel.

FIG. 5 illustrates three examples of lumen segmentation results, shown as boundary 43, in rectangular view obtained by applying a dynamic programming scheme. FIG. 5A exhibits a vessel in contact with the guide wire. FIG. 5B exhibits a vessel with side branches. FIG. 5C exhibits a vessel with stents.

Lumen Quantification

Figure 6:
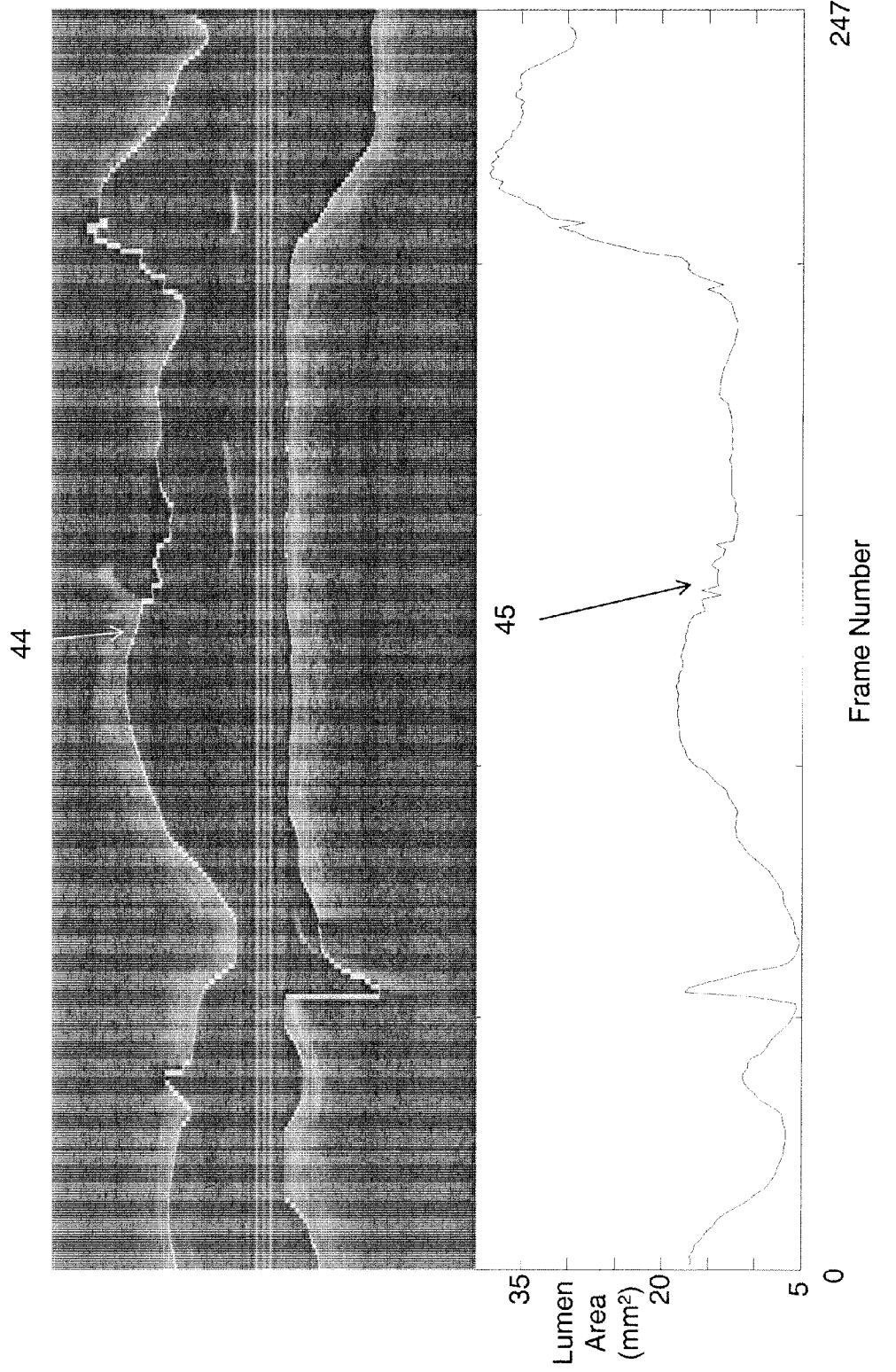
FIG. 6 illustrates a longitudinal cut view of the segmented lumen of a blood vessel and an associated plot of the lumen area per frame.

Lumen area information can be used clinically to estimate the extent of coronary artery stenosis and guide interventional procedures. Based on lumen segmentation results along the entire pullback, in lumen quantification step 33, a plot 45 of the lumen area against the frame number can be created, for example as shown in the lower portion of FIG. 6. The upper portion of FIG. 6 shows is the longitudinal cut view of the segmented lumen, represented by the boundary line 44, of the same vessel represented by the lumen area plot 45 in FIG. 6. While the system and methods described above in connection with lumen segmentation step 32 and quantification step 33 are made with reference to 2D input data, 3D input data may also be used.

Guide Wire Segmentation

With reference to FIG. 2, the guide wire is highly reflective and manifests itself in OCT images as a bright body 21 protruding into the lumen with a long shadow 22 behind it. The guide wire segmentation technique exploits these two characteristics. It can be seen that the guide wire shadow is a gap in the BSL. If more than one gap is present (e.g. a side branch), then the gap with the brightest pixels (guide wire body) along the A-lines within the gap is considered to be the guide wire shadow. If the guide wire is misidentified in an individual frame, the detected guide wire position of individual frames can be reconciled by morphological opening along the longitudinal direction.

After guide wire is detected, the A-scans corresponding to shadow 22 are excluded for further analysis.

Figure 7:
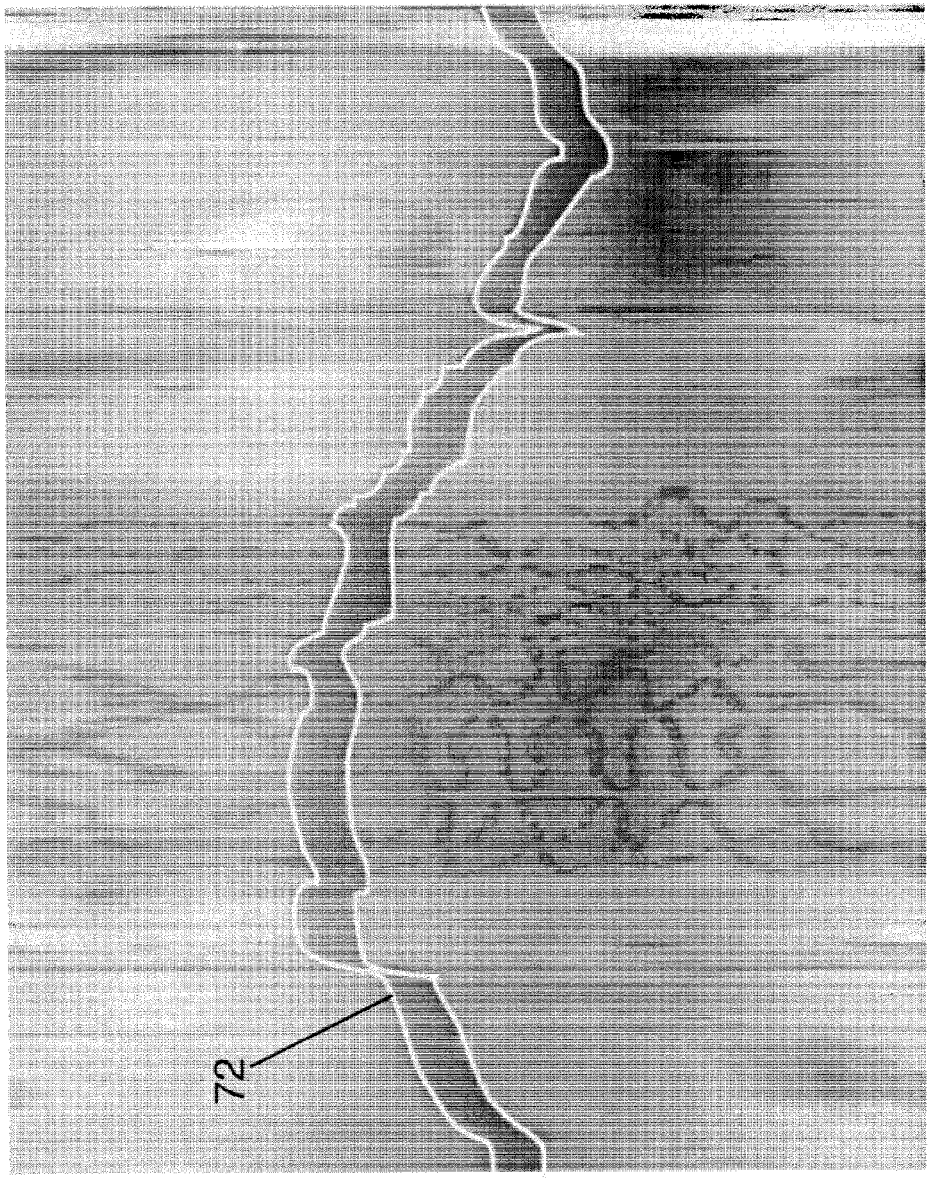
FIG. 7 illustrates a longitudinal image of a stented vessel based upon pixels of individual A lines.

While the system and methods described above in connection with guide wire segmentation step 34 are made with reference to 2D input data, 3D image data may also be used. In one embodiment, guide wire segmentation can also be performed in longitudinal view or in 3D space. To perform in longitudinal view, all the pixels of individual A scans are added together or averaged so one frame becomes one line and the entire pullback containing many frames becomes one longitudinal image. FIG. 7 illustrates an example of the longitudinal image of a stented vessel after adding up pixels of individual A lines. The regions of guide wire shadow, marked by boundary 72, are darker compared to surrounding tissues. The border of the guide wire shadow can be segmented by dynamic programming or live wire along the longitudinal image and then mapped back to individual frames. To perform in 3D space, edge detectors such as the Canny edge detector may be used to extract the longest edges along the longitudinal direction.

Vessel Wall Segmentation

An aim of the vessel wall segmentation step 35 is to find the regions of interest where plaque may exist. Plaques including macrophages mainly appear in the intima layer of the arterial vessel wall. In plaque regions such as lipid plaque 80 and calcified plaque regions 23 shown in FIG. 2, usually the media or adventitia layer cannot be seen because of the attenuation of light by the plaques. In some instances, however, the media and adventitia can appear in non-plaque or fibrous plaque areas, as shown by reference to the adventitial 48 in FIG. 2. The heterogeneous texture of the adventitial tissue can be used to facilitate vessel wall segmentation.

In one embodiment, a texture-based active contour method may be implemented to find the boundary of the adventitial tissue as the vessel wall. The original gray-scale intensity image is mapped onto a texture feature space T that magnifies the difference between the adventitial tissue and the inner layer of the arterial wall. In one application of the texture mapping, a Gabor filter is chosen. The Gabor filter can be tuned to different spatial frequencies and orientations, which is suitable for extraction of the adventitial tissue, which exhibits texture featured by rapid oscillations of intensity values along the light propagation direction. The Gabor filter is basically an oriented complex sinusoidal modulated by a 2-D Gaussian kernel, an example of which may be given as follows:

$$G(x, y) = \frac{1}{2\pi\delta_x\delta_y}\exp\left[-\frac{1}{2}\left(\frac{x}{\delta_x}\right)^2 - \frac{1}{2}\left(\frac{y}{\delta_y}\right)^2\right]\exp[2\pi \text{ if } (x\cos\theta + y\sin\theta)].$$

The terms $\delta_x$ and $\delta_y$ are the scales for smoothing the Gaussian kernel, $\theta$ is the orientation angle and f is the spatial frequency. The Gabor filter is convolved with the original rectangular image, and the root mean square of the real and imaginary parts of the resulting convolution provides the desired Gabor representation of the image for one of the selected orientations. In one implementation, $\delta_x$ and $\delta_y$ are chosen to be 10 (pixels), f is chosen to be 1 (pixel) and $\theta$ ranges from between $\pi/3$ to $2\pi/3$ in increments of $\pi/12$, resulting in 5 different Gabor representations along each of the 5 orientations. A vector-based active contour model may be used to integrate the 5 Gabor representations. Principle Component Analysis or "PCA" may be used to transform nonorthogonal Gabor representations into an uncorrelated feature space. By implementing PCA, the number of polar transformations may be reduced without sacrificing the accuracy of the segmentation. For example, the first PCA transformation may contains approximately 75% of the original feature space information and may be chosen as the sole texture image representation.

Figure 8:
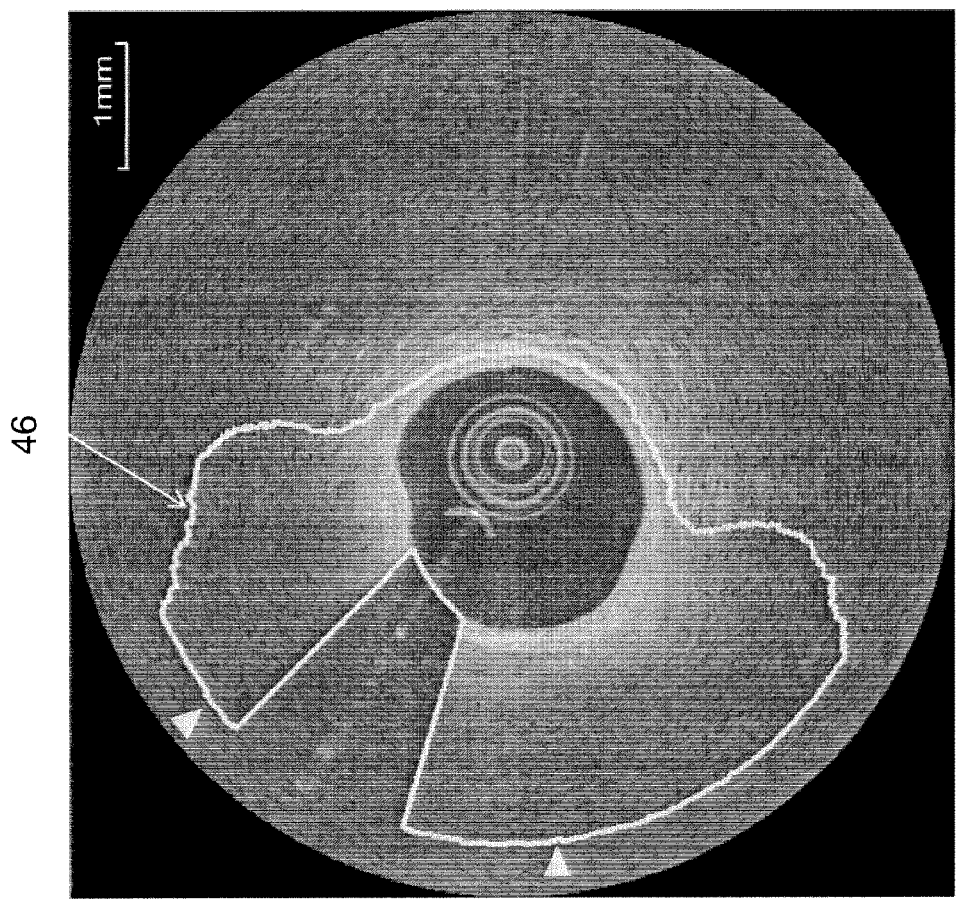
FIG. 8 illustrates an OCT image of a coronary artery having a segmented vessel wall using an active contour method.

The initial contour for the vessel wall segmentation step 35 is chosen as the boundary of the lumen determined in the lumen segmentation step 32. The contour then grows and evolves based on the texture information of the image. Parts of the moving contour facing no texture difference will keep growing while leaving the parts of the contour that have reached the boundary stationary. The contour finally stops at the boundary where the texture difference between the region outside and inside the contour is maximized, corresponding to the boundary of the adventitial tissue. The entire contour is stopped when there is little change of the texture difference inside and outside the contour within a predefined layer having a width of w where w is chosen to safely cover the depth of all calcified plaques. In one implementation, w is set to 2 mm, corresponding to the contour depth limit of an example OCT system, for example as shown by the arrowheads in FIG. 8. The segmented arterial wall boundary 46 is shown in FIG. 8. The framework for an exemplary active contour method is discussed more fully below with respect to the calcified lesion segmentation step 36. This active contour approach is based on Chan-Vese active contour model without edges as described in Chan, T. F., and Vese, L. A., Active Contours Without Edges, IEEE Transactions On Image Processing, Vol. 10, No. 2, pp. 285-96, February 2001, and Vese, L. A. and Osher, S. J., Modeling Textures with Total Variation Minimization and Oscillating Patterns in Image Processing, Journal of Scientific Computing, Vol. 19, Nos. 1-3, pp. 553-72, December 2003 incorporated herein by reference. In addition to an active contour approach described herein, other suitable methods for closed contour segmentation may also be used.

In another embodiment, vessel wall segmentation can be obtained by searching the adventitia boundary using a dynamic programming approach similar to that in lumen segmentation. One difference is the energy function, which is defined as the standard deviation difference of the left and right side region of the corresponding pixel in the rectangular view. Pixels inside the lumen will have zero energy. This method can accurately delineate the adventitia boundary if it is present, and make a smooth contour when the adventitia is not seen. Further classification of the tissue behind the contour may be performed to differentiate the part of contour behind which no adventitia exists. Limitations of a particular OCT device may prevent determination of the boundary of the adventitia. This limitation may be circumvented by creating an artificial boundary to safely include coronary plaques for further segmentation (e.g. steps 36 and 38) or for automatic tissue characterization. In one such embodiment, this artificial boundary is generated automatically by moving the contour to a certain depth (e.g. 2 mm) to safely cover all the plaques. In another embodiment, the artificial boundary is generated semi-automatically by manually dragging the contour through the use of an input device 19 to the desired position with the connected contour in adjacent frames corrected correspondingly by interpolation. The boundary identification methods described above are merely exemplary, and other boundary identification methodologies may be implemented to identify a suitable boundary.

Figure 9A:
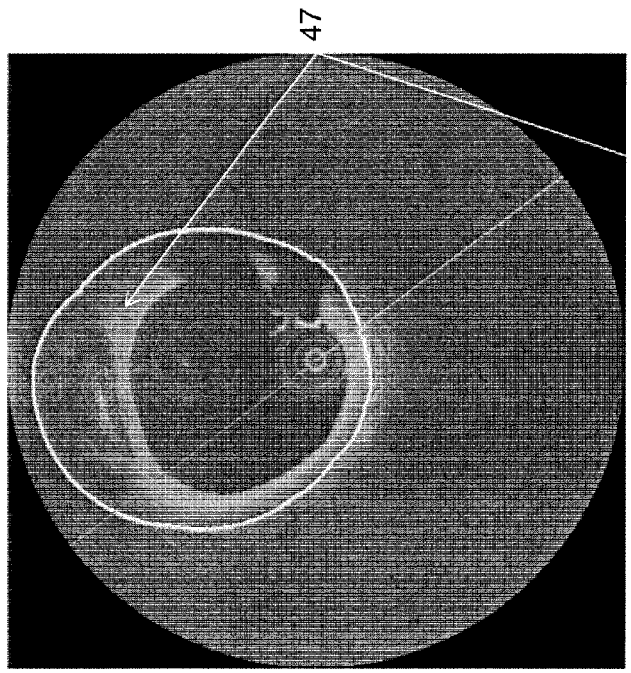
FIGS. 9A and 9B illustrate a cross sectional OCT image and a corresponding longitudinal view, respectively, showing a segmented vessel wall using a dynamic programming method.
Figure 9B:

FIGS. 9A and 9B illustrate the vessel wall segmentation results using dynamic programming in both longitudinal and cross-sectional views, respectively. The contour can be smoothed in 3D space to mimic the real biological boundary. The region 47 between the adventitia and lumen boundary is the region of interest for searching for calcified plaques.

While the system and methods described above in connection with vessel wall segmentation step 35 are made with reference to 2D input image data, 3D input image data may also be used. For example, vessel wall segmentation may also be performed in 3D space using 3D active contours considering the 3D texture of the adventitia tissue. In this way, the segmented contour will be continuous (smooth) in a 3D volume giving a smooth surface.

Calcified Plaque Localization—Flow Chart

Figure 10:
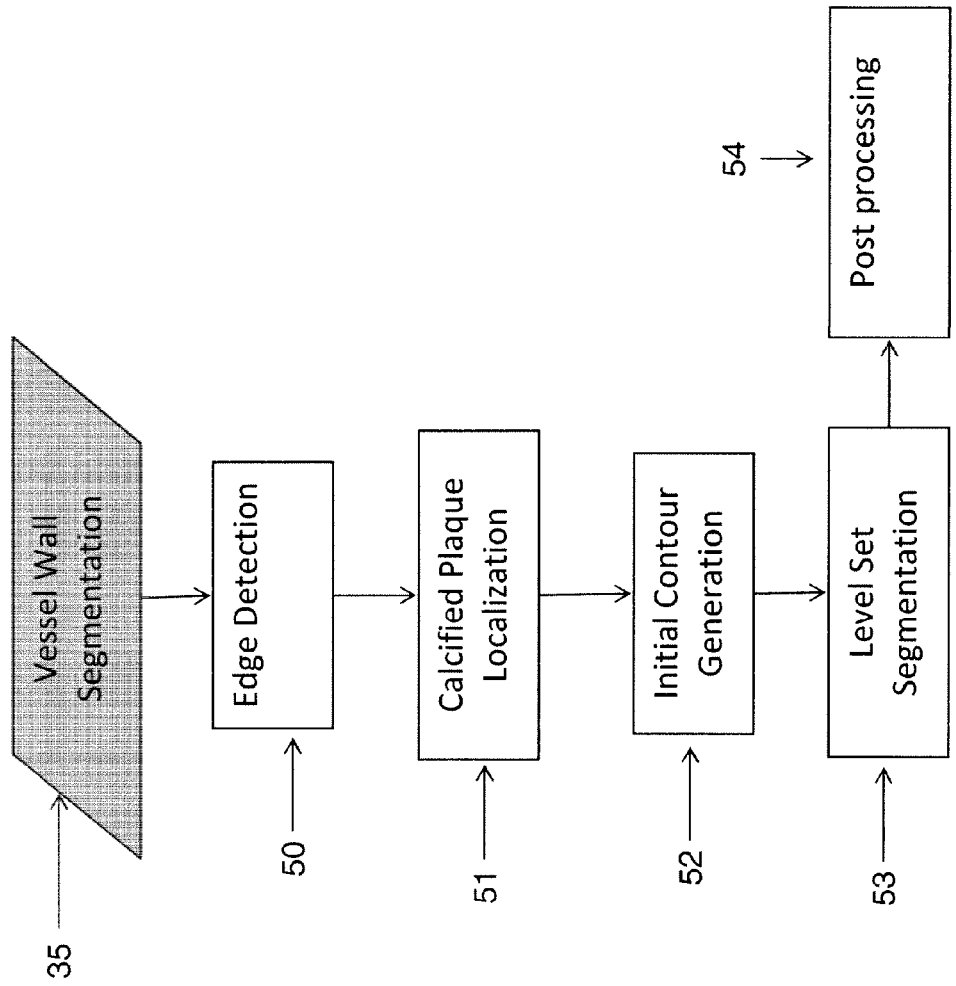
FIG. 10 illustrates an example calcified plaque segmentation method.

Calcified plaque segmentation and quantification can be used to estimate the distribution of superficial calcification and inform strategies for optimal placement of coronary stents. FIG. 10 illustrates an example method for the calcified plaque (CP) segmentation step 36 shown in FIG. 3. Taking the segmented vessel wall from step 35 as the region of interest, CP is localized by first performing edge detection step 50, and then in calcified plaque localization step 51, localizing the vessel wall that can capture the edge aggregations. In the initial contour step 51, an initial contour is generated from the binary edge image and the contour evolves towards the CP boundary based on a level set model applied in level set segmentation step 53. Level set segmentation step 53 may be followed by a post-processing step 54, which may involve correction of calcified lesions truncated by guide wire shadows, and labeling of plaques, for example.

Calcified Plaque Edge Detection

The CP edge detection step 50 serves two purposes. One is to provide a gradient image for the active contour model applied in level set segmentation step 53, and another is to provide a binary edge mask for calcified plaque localization step 51.

Edge detection of CP may be performed by distinguishing 2 types of edges of a CP in a rectangular intravascular OCT image. With reference to FIG. 2, these edges are the inner border ("IB") 24 and outer border ("OB") 25. These names indicate the edge location with respect to the lumen. IB 24 is near to the lumen and usually strong and easy to identify. OB 25 is far from the lumen and is usually weak and relatively more difficult to identify. The common feature of the two types of edges is their sharp borders delineating the plaque. Before the CP edge detection, the original image may be convolved by a filter such as a median filter, or a Gaussian filter, or a Wiener filter to reduce speckle noise. The CP edge detection may be performed sequentially. In one such approach, the strongest IB 24 is detected first. Second, the location of the IB 24 is used as prior information to detect the weak OB 25.

Figures 11A, 11B, 11C:
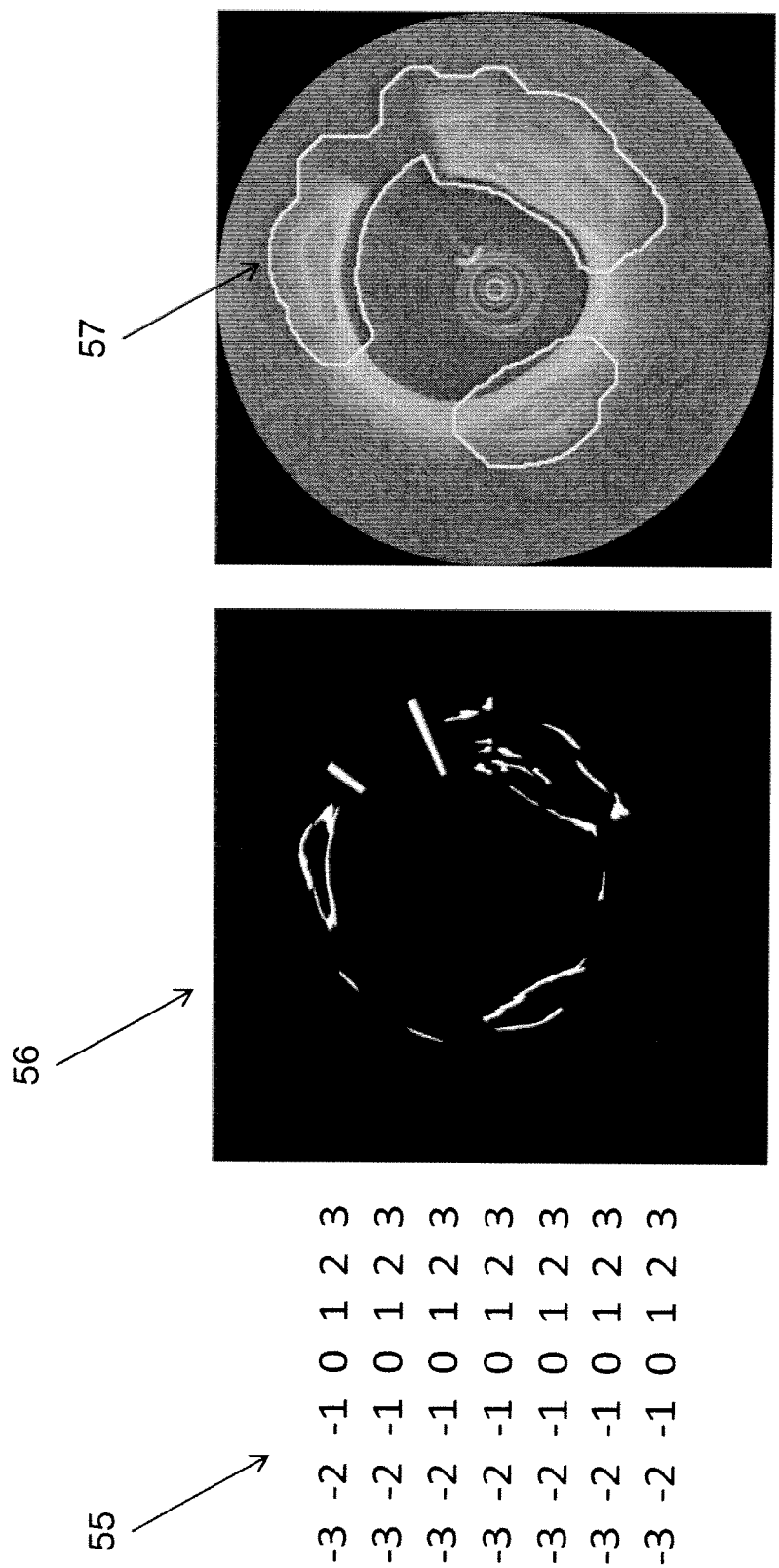
FIG. 11A illustrates an example matched filter for calcified plaque edge detection.
FIGS. 11B and 11C illustrate results of an edge detection process from the matched filter shown in FIG. 11A, and a corresponding initial contour, respectively.

A matched filter 55, such as the specially designed matched filter shown in FIG. 11A, may be used to detect the edges. This matched filter 55 has a similar shape as the calcium edge and is expected to give strong response wherever there is a lesion, but produces weak response in presence of diffuse edges. The filter is also direction sensitive, so IB 24 and OB 25 may be detected by the same filter 55 rotated by different angles. As a seven-by-seven matrix, the matched filter 55 is not ideal for application to extremely superficial IB 24 with depth smaller than the size of the filter. In such cases, an alternative small directed edge mask such as a Prewitt operator (3-by-3) may be used. The CP edge detection may be confined to the region 46 or 47 shown in FIGS. 8, 9A and 9B. Other matched filters may be used, for example, in order to reduce response to extraneous image elements.

In one application, the matched filter 55 is rotated from $-\pi/12$ radians to $\pi/12$ radians relative to the incident light from the catheter 16 in increments of $\pi/36$ radians in order to detect oblique IB 24 along different directions. The maximum response at each pixel among the convolution results for different angles is set as the final gradient value for that pixel, thereby generating a gradient image. A binary edge mask is generated by hysteresis thresholding as discussed, for example, in Canny, J., A Computational Approach to Edge Detection, Readings in Computer Vision: Issues, Problems, Principles and Paradigms, p. 184-203, 1987, incorporated herein by reference. To detect OB 25, the matched filter is rotated by $\pi$ radians and convolved with the original image only in areas behind detected IB 24. The final gradient image and binary edge image are obtained by combining the individual responses from IB and OB. FIG. 11B illustrates an example of CP edge detection result 56.

Thresholding may generate false positive edges. False positive IB edges can be removed by a further classification based on the edge features, including but not limited to, the edge sharpness and the intensity of the tissue behind the edge. Edge sharpness can be described by the slope of the A-line segment across the edge. In one implementation, the slope of the 0.08 mm A-line segment across the IB, and the average intensity of the region about 0.16 mm behind the IB are chosen as features for edge classification. Classification is performed using decision trees, which are described in the discussion of macrophage segmentation step 38.

Calcified Plaque Localization

The CP localization step 51 locates the calcified lesion at a coarse level. After the calcified plaque edge detection step 50, there may still be non-calcium false edge fragments present in the binary edge image BW due to thresholding. Since the true edges of a calcified plaque are always aggregated together creating the boundary of a calcified plaque, an edge fragment observed as isolated in the calcified plaque edge detection step 50 is less likely to be part of the boundary of the calcified plaque. One way to locate edge aggregations is to select the segment of the vessel wall that could capture the edge aggregations. In one embodiment, once the binary edge areas within a 40 degree segment of the segmented vessel wall 46 or 47 as shown in FIGS. 8, 9A and 9B, exceeds a threshold of 0.02 mm$^2$, the segment is marked as initial ROI. The segment length is increased until there is no change in edge intensity and stored as the final ROI for the CP.

Calcified Plaque Contour Initialization

The CP segmentation is based on an active contour approach step or level set segmentation step 53 that requires an initial contour $C_0$. In the initial contour generation step 52, $C_0$ may be created from the polar representation of binary edge image within the ROI by use of morphological dilation, thereby eliminating the need for manual contour initialization. However, contour initialization may also be done manually. FIG. 11C illustrates the initial contour 57 generated from FIG. 11B.

Calcified Plaque Segmentation Based on an Active Contour

With reference to FIGS. 2 and 10, the CP segmentation step 36 utilizes an active contour model based on a level set approach in step 53. The level set approach allows for the representation of a 2D contour as a zero level set of a 3D surface.

In one embodiment, $\phi$ is defined as a signed distance function, or "SDF," with a zero level curve represented by C={(x, y)|$\phi$=0}. The curve C is bounded in the region $\Omega \subset R^2$, and $\phi$ satisfies: $\phi$=0 on the boundary of C, $\phi$<0 outside C and $\phi$>0 inside C. Starting with the initial contour $C_o$, the curve C is driven by minimizing the following energy term to the desired calcified lesion boundary:

$$E = \mu \int_Q \frac{1}{2}(\nabla\varphi - 1)^2 dxdy + \lambda \int_Q g'\delta(\varphi)|\nabla\varphi|dxdy + v\int_Q g' H(-\varphi)dxdy +$$
$$\kappa\left(\int_Q |I_0(x,y) - c_1|^2 H(\varphi)dxdy + \int_Q |I_0(x,y) - c_2|^2 (1 - H(\varphi))dxdy\right)$$

For a numerical implementation of the level set approach, reference may be made to Li, C., et al. Level Set Evolution without Re-initialization: A New Variational Formulation. IEEE International Conference on Computer Vision and Pattern Recognition (CVPR), 2005, San Diego, incorporated herein by reference. The term $\delta(\phi)$ is a 2D Dirac function. H($\phi$) is the Heaviside function, with H($\phi$)=1 if $\phi \geq 0$ and H($\phi$)=0 if $\phi$<0. $I_0$ is the original polar transformed image after guide wire correction, g'=1/(1+g) where g is the gradient image generated during the calcified plaque edge detection step 50, $c_1$ is the average intensity value inside C, while $c_2$ is the average intensity in a small ring surrounding the curve C. In the original Chan-Vese approach, the term $c_2$ is the average intensity of the entire area outside the curve C. A global energy minimum may be found by using such an approach. However, such a global minimum is unnecessary as the desired initial contours have already been localized. Thus, the CP segmentation step 53 may seek a local minimum by focusing the active contour in a small region around the initial contour, with the local minimum corresponding to the boundary of the calcified lesion. The terms $\mu$, $\lambda$, $v$ and $\kappa$ are weighting terms. The first term of the energy equation stabilizes the evolution of the curve. The second term is a length term regulating the smoothness of the evolving contour. The third term is an area term governing whether the curve will grow or shrink, and the speed of the moving curve. This term is set to a positive value to shrink the contour toward the calcified lesions. The fourth term contains the region-based intensity information of the original image. Notice that the gradient information is involved in the weighted length term and area term. By minimizing the total energy term E, the contour is driven toward the desired calcium boundary where the gradient is maximized, and the intensity difference between the regions outside and inside the boundary is also maximized.

A similar energy term may be implemented in the vessel wall segmentation step 35 described above. There, the term g', which contains the gradient image term g, is removed from the energy term, and $I_0$ is replaced by T, the texture feature space after Gabor filtering. Further, the initial contour is chosen as the lumen border obtained in the lumen segmentation step 32. Finally, the coefficient for the area term is set negative in order to grow the contour.

Figure 12B:
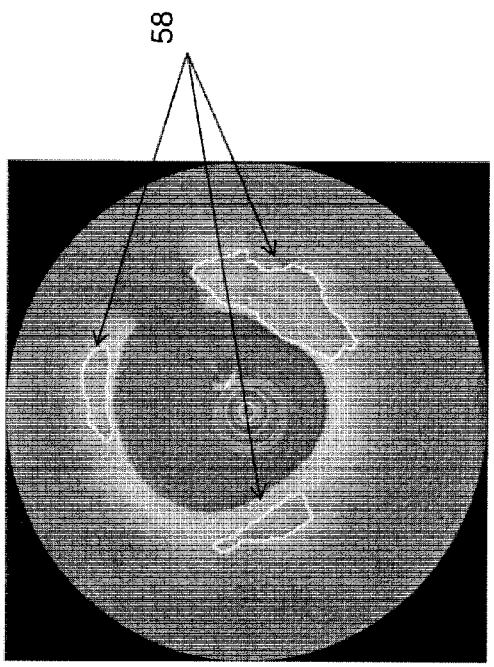
FIG. 12A-D illustrate example OCT images with and without contours indicating segmented calcified plaques.
Figure 12D:
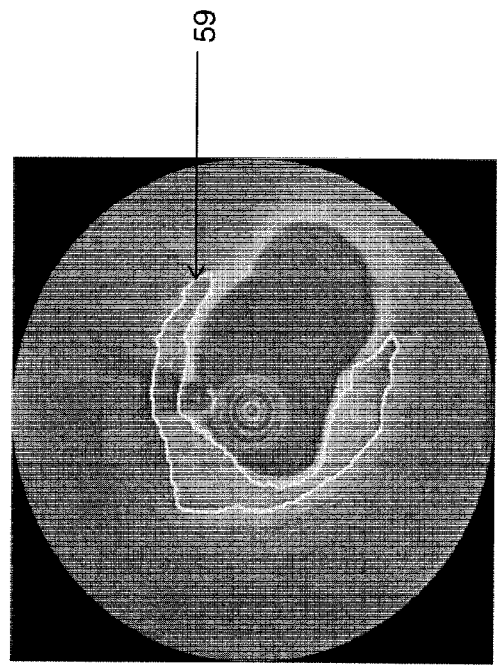
Figure 12A:
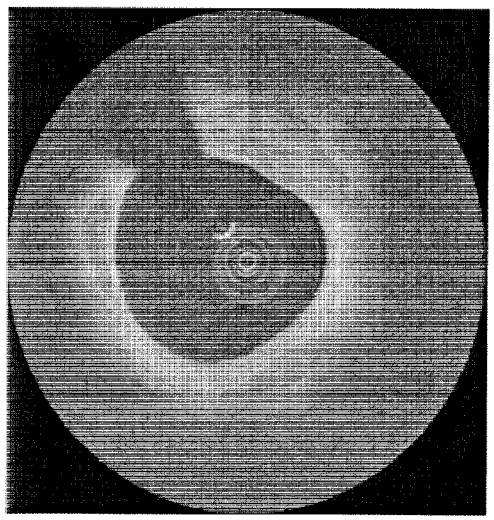

To prevent the contour from passing the desired boundary, in particular weak edges, the level set segmentation step 53 may include a stopping criterion based on the contour evolution speed and the boundary location. According to one such criterion, the contour is stopped if it both hits the boundary 56 identified in CP edge detection step 50 and shown in FIG. 11B, and at the same time has a speed close to zero. In one implementation, the speed for stopping the contour is set as 0.001 mm$^2$/iteration. For images containing multiple CPs, the stopping criterion may be met for one plaque but not for others. This can lead to insufficient segmentation for other plaques unless contours are permitted to evolve independently. In one implementation of method 36, the calcified plaque segmentation step 53 may include a multi-scale process to decouple the evolving contours. Using this approach, the starting contour $C_0$ is not initialized as one SDF but as n SDFs, where n represents the number of separate initial contours. Each of the n SDFs uses the same parameters defined above and has its own life cycle. In addition, due to the flexible topology of the level set and the positive value of the area term, existing SDFs may break into multiple separate contours. In such case, each separate contour is reinitialized into a daughter SDF and begins its own life cycle. Additionally, the stopping criterion for every SDF is evaluated separately. In another aspect of the level set segmentation step 53, any very small SDF islands, for example less than 0.02 mm$^2$ will be removed as such calcified lesion are typically of little clinical relevance. FIGS. 12A and C illustrate two OCT images, and FIGS. 12B and 12D illustrate the same OCT images showing CP segmentation results as boundaries 58 and 59.

Figure 12C:
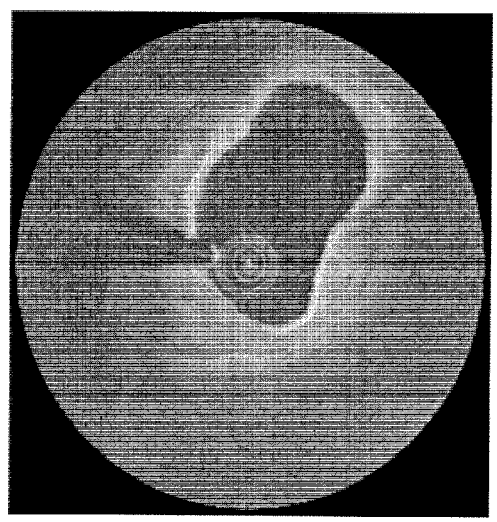

With reference to FIG. 10, the level set segmentation step 53 may be followed by a post-processing step 54, which may involve correction of calcified lesions truncated by guide wire shadows. In a typical case, regions identified as calcium lesions appear on either side of a shadow, for example as shown in FIG. 12C. In such a case, the gap may be filled-in by interpolation based on the assumption that the lesions are part of a single lesion spanning the area covered by the guide wire shadow. In addition to an active contour using a level set approach described herein, other suitable methods for closed contour segmentation may also be used.

The post-processing step 54 may also involve a process to correct wrongly segmented calcified lesions. This may involve removal of incorrectly segmented regions based on information contained in adjacent segmented frames. It is unlikely for a calcified lesion to appear in only a single frame. As such, the post-processing step 54 may involve removal of lesions in a particular frame when the particular lesion has no overlap with lesions segmented in the immediately adjacent frame or frames. The CP segmentation may still generate false positives. False positives may be manually removed such that the calcified plaque segmentation step 36 becomes semi-automatic. A fully automatic approach may also be adopted by performing post classification to the segmented regions.

Additional Calcified Plaque Segmentation Techniques

In other embodiments, a supervised semi-automatic method can be utilized to more precisely segment the calcified plaques. In one such embodiment, such as the live-wire approach described in A. X. Falcao, J. K. Udupa, S. Samarasekera, S. Sharma, B. E. Hirsch and R. d. A. Lotufo, "User-Steered Image Segmentation Paradigms: Live Wire and Live Lane," Graphical Models and Image Processing 60(4), 233-260 (1998), incorporated herein by reference. Live-wire can be used to accurately segment the calcified plaque boundary in a frame-by-frame manner. It is possible to propagate the segment result in the current frame to the following frames by combining the live wire with the methods described herein. In one embodiment, the segmentation result in the current frame can be used to select the calcified plaque edges in the following frames to reduce false positive edges.

It is understood that 3D extensions of methods described above exist. The level set segmentation can be extended to 3D and the corresponding energy function will be all defined in 3D. Potential advantages of a 3D method are additional robustness to gross segmentation errors, avoidance of small errors due to a lack of image evidence or artifact in one frame, and/or creation of a calcification blobs in 3D along the vessel. A 3D approach is not always advisable in the case that structures such as calcifications are small relative to the spacing between 2D acquisitions as would be obtained in the event of a "fast" pull back velocity at a fixed A-line data rate.

In another embodiment, segmentation of calcified plaques can be performed by using graph cut algorithms, such as disclosed in Y. Y. Boykov and M. P. Jolly, "Interactive graph cuts for optimal boundary & region segmentation of objects in ND images," in International Conference on Computer Vision, pp. 105-112 (2001), incorporated herein by reference. In one such embodiment, the volumetric OCT images can be transformed into a graph with each node representing each volumetric pixel, or "voxel," of the original data. For each node in the graph, we assign an N-link representing the edge between neighboring elements, and a T-link representing the edge connecting the node to the terminal. The N-linking edge weight is the edge strength between adjacent elements, determined from the edge detection step and normalized by the three dimensional distance between the elements. The T-link edge weight represents the probability of the element belonging to "object" or "background." A priori information may be used as the hard constraint to guide the construction of the T-link. The edges of the graph describe the connections between adjacent pixels taking consideration of the smoothness and connectedness of the 3D surface of the calcified plaques. The optimum segmentation is equivalent to finding the optimum graph cut such that the total cost of the cut is minimized. The minimum cut of the graph can be found by using standard Ford-Fulkerson algorithm, such as described in Ford, L. R.; Fulkerson, D. R. (1956). "Maximal flow through a network". Canadian Journal of Mathematics 8: 399-404, incorporated herein by reference, or a faster "max-flow" algorithm developed by Boykov and Kolmogorov, and described in Boykov, Y. and V. Kolmogorov, An experimental comparison of min-cut/max-flow algorithms for energy minimization in vision. Pattern Analysis and Machine Intelligence, IEEE Transactions on, 2004. 26(9): p. 1124-1137, incorporated herein by reference.

As for the graph cut algorithm, a semi-automatic approach can be adopted to extract the CP edges. In one embodiment, the users input an initial mask inside the CP on selected frames of a single lesion. The missing masks between input frames will be interpolated. The optimum frame interval for user input will be tested. In another embodiment, the users may directly input an initial volume ROI inside the CP in 3D, and the ROI is mapped back to individual frames. All the pixels inside the masks in individual frames can be used as priori information for graph cut segmentation. At the same time, the edge detection can be performed as in step 50. In another embodiment, the edge detection can be performed in an inside-out direction in the corresponding rectangular view. A 2D matched filter, designed based on the profile of CP edges from some training data, can be convolved with the A lines pointing from the centerlines of the mask (inside CP) to the surrounding regions outside CP. The luminal edge and abluminal edge of CP can be specifically captured using this inside-out matched filter detection.

Another facet of the post-processing step 54 is to label segmented lesions. Any labeling scheme must be systematic and consistent in order to aid in interpretation and validation of results of the method 36. In one such scheme, the longitudinal relationship between lesions in adjacent frames is accounted for by labeling overlapping lesions in adjacent frames as the same lesion. This labeling may occur in a two-step process. Initially, in step (a), all segmented calcified lesions within a volumetric image set are unlabelled. We initialize the total number of lesions as TL=0. Starting with the first frame, n=1, and starting from 12 o'clock and proceeding clockwise, the segmented lesions are labeled as $Ca_{1+TL}$, $Ca_{2+TL}$, ... $Ca_{m+TL}$ (where ai=i) for m unvisited segmented lesions in the current frame. For every lesion $Ca_{i+TL}$, step (b) is executed and $Ca_{i+TL}$ is marked as visited. If all the lesions in the current frame are visited, we update TL=TL+m and n=n+1. In step (b), starting from 12 o'clock and proceeding clockwise again in the next frame p+1, where p=n, any lesion found to be longitudinally connected or overlapping with $Ca_{1+TL}$ for a given i and TL is also labeled $Ca_{i+TL}$, and marked as visited. Then, p is updated to equal p+1, the procedure in (b) will be repeated until no lesion connected with $Ca_{i+TL}$ is found in an adjacent frame, then step (a) is executed until all the frames are evaluated. By using these steps, the longitudinally connected lesions are labeled as one lesion, and other unconnected lesions are labeled both in a clock wise order and a temporal or longitudinal order.

Calcified Plaque Quantification

Figure 13:
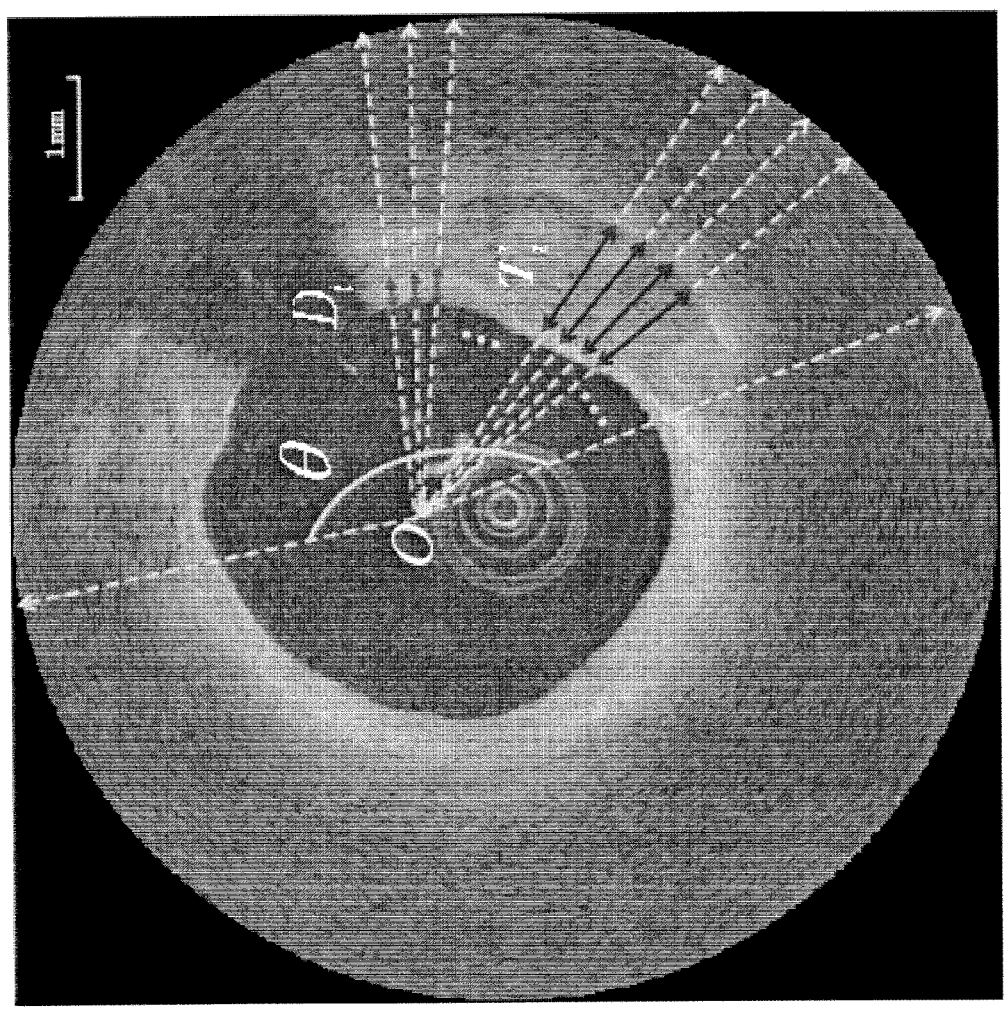
FIG. 13 illustrates an example OCT image showing measurement parameters that may be used in quantification methods for calcified plaques.

Once the calcified plaque is segmented and labeled, a quantification step 37 may be performed. Five quantitative measures, the depth, area, thickness, angle fill fraction (AFF) and volume may be calculated automatically. The area is calculated by counting the number of pixels inside the CP weighted by the area per pixel, which can be obtained, for example, by identifying the scanning range of an OCT system. The depth, thickness and AFF are all calculated with reference to the centroid (indicated by O in FIG. 13) of the lumen for each individual CP. FIG. 13 illustrates the methodology. The depth and thickness are defined as $$\text{Depth} = \frac{1}{n}\sum_i^n D_i$$

$$\text{Thickness} = \frac{1}{n}\sum_i^n T_i$$

Where n is the maximum number of the non-overlapping rays radiating from O spanning across the CP, and $D_i$ and $T_i$ are the ith depth and thickness, respectively. The AFF θ is the largest angle between the spanning rays. The volume of the CP is calculated by multiplying the sum of the areas of individual CPs of the same label with the frame interval.

While the system and methods described above in connection with calcium plaque segmentation step 36 and quantification step 37 are made with reference to 2D input data, 3D input data may also be used. For example, in an alternative embodiment, edge detection 50 is conducted using 3D edge detectors, localization is performed in the whole volume of the vessel wall, and initial surface is generated by morphological dilation of the binary edge mask in 3D coordinate. 3D level sets extended from the 2D model discussed above may be used for contour evolution. It is understood that potential advantages of a 3D method are additional robustness to gross segmentation errors, avoidance of small errors due to a lack of image evidence or artifact in one frame, and/or creation of a calcification blobs in 3D along the vessel. A 3D approach is not always advisable in the case that structures such as calcifications are small relative to the spacing between 2D acquisitions as would be obtained in the event of a "fast" pull back velocity at a fixed A-line data rate.

Macrophage Segmentation

Figure 14:
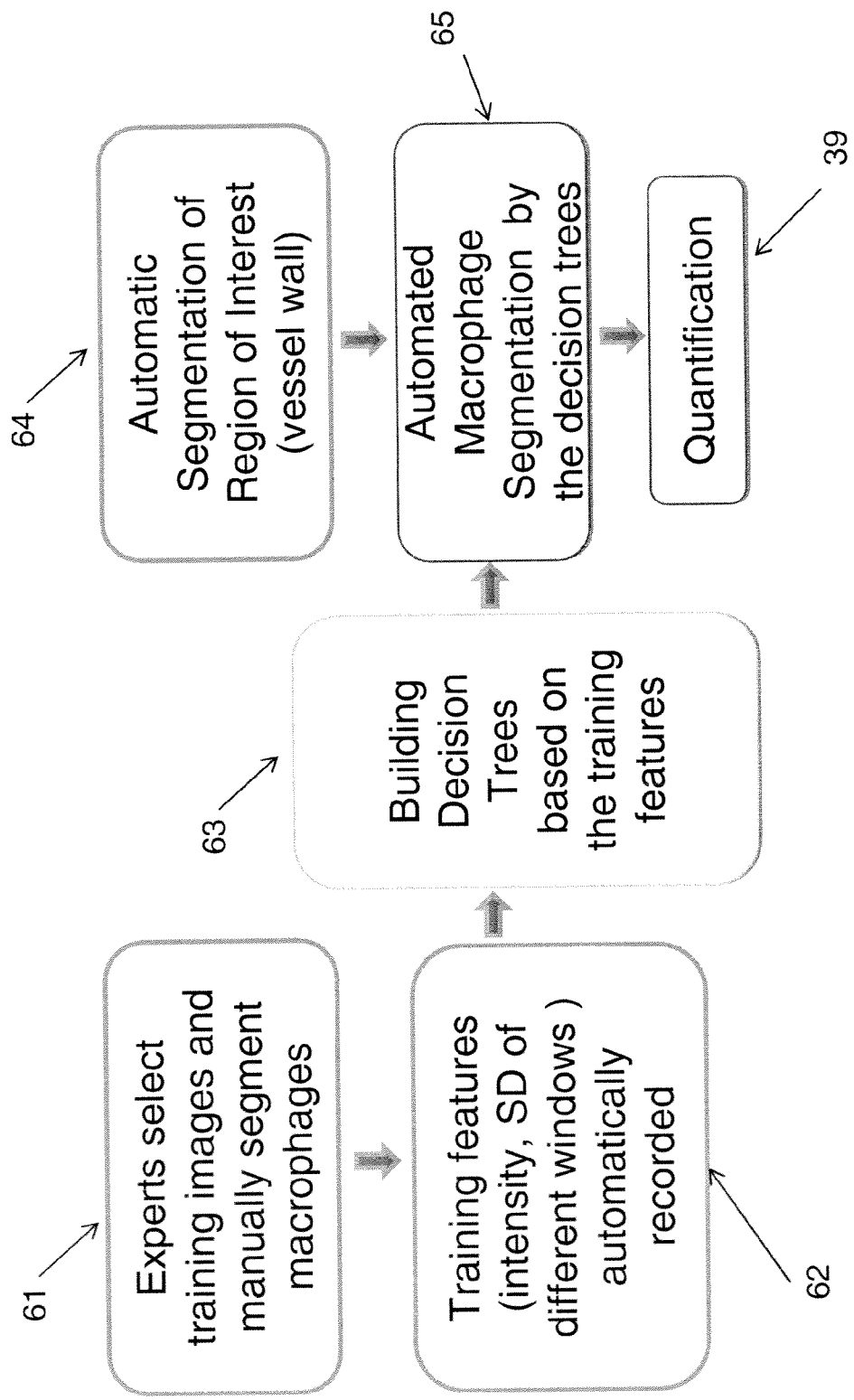
FIG. 14 illustrates an example method for segmentation of macrophages.

Quantification of macrophages can aid diagnosis and prediction of unstable plaque and associated acute coronary events. In human coronary arteries, macrophages 70 within the fibrous cap of the lipid plaques are hypothesized to be bright spots under OCT. In atherosclerotic ApoE$^{-/-}$ mice, they are more prominent bright spots found in superficial aorta layer. FIG. 14 illustrates an example method to segment and quantify macrophages in ApoE$^{-/-}$ mice aorta. The method considers the pixel intensity and standard deviation of surrounding windows of different sizes to classify individual pixels as macrophages or not. The methods discussed herein in relation to mouse aorta may also be extended to human data.

With reference to FIG. 14, the method utilizes a supervised approach in that experts or supervisors first select some training images and manually segment the macrophages for further use in step 61. The training images are ideally of good quality and can be registered with mac-3 stained histology 69 such that they can be used as the reliable training source. In one implementation, 60 training images from 12 mice (5 per mouse) at different ages fed by an atherosclerotic diet are used. From the manual segmentation results, intensity and standard deviation of different size windows are recorded as the training features in step 62. Training as described herein can be done during the manufacturing process, and need not be performed, for example, individually for each system 10.

Macrophage classification is performed using decision trees 63. The parameters of the decision trees are automatically determined by the training features, thereby avoiding subjective parameter selections. When the method is used in other OCT machines or to human data, only the training images need to be selected again, the decision trees will be built automatically based on the new training sets. There are many types of decision trees may be considered. In one embodiment, J48 pruned decision trees provided by Weka, a machine learning software, is utilized.

Figure 15C:
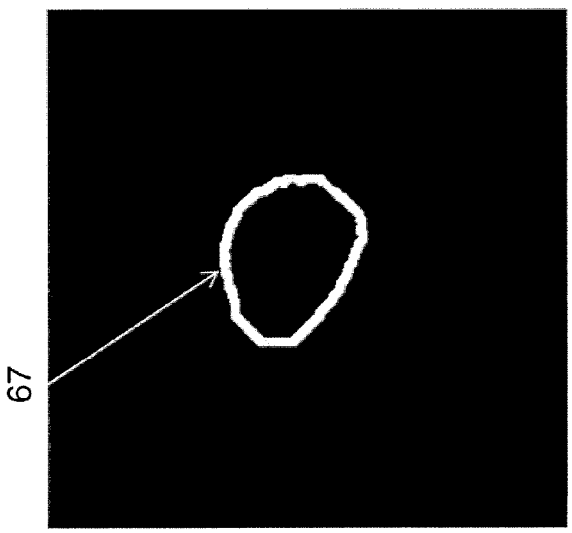
FIG. 15A-C illustrates an example original OCT image of a mouse aorta, the resulting lumen segmentation of the image in FIG. 15A, and the resulting region of interest containing macrophages, respectively.
Figure 15B:
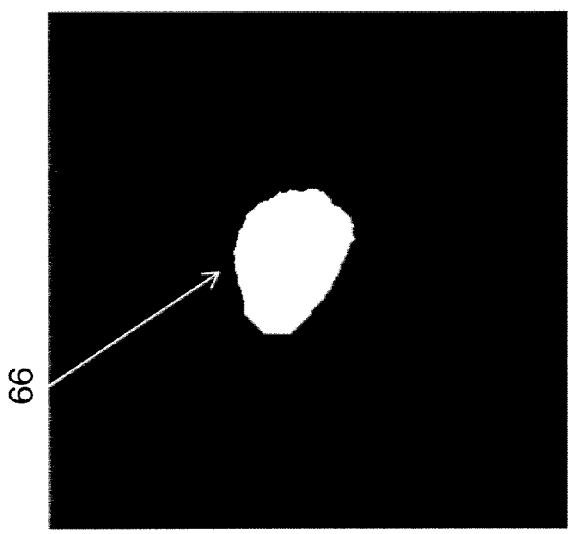
Figure 15A:
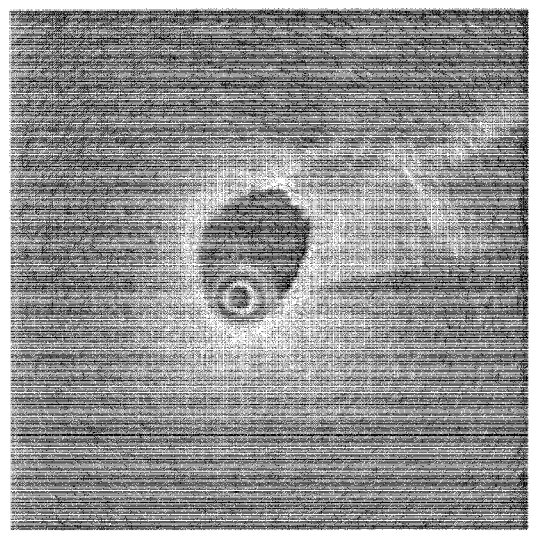
Figures 16A, 16B, 16C:
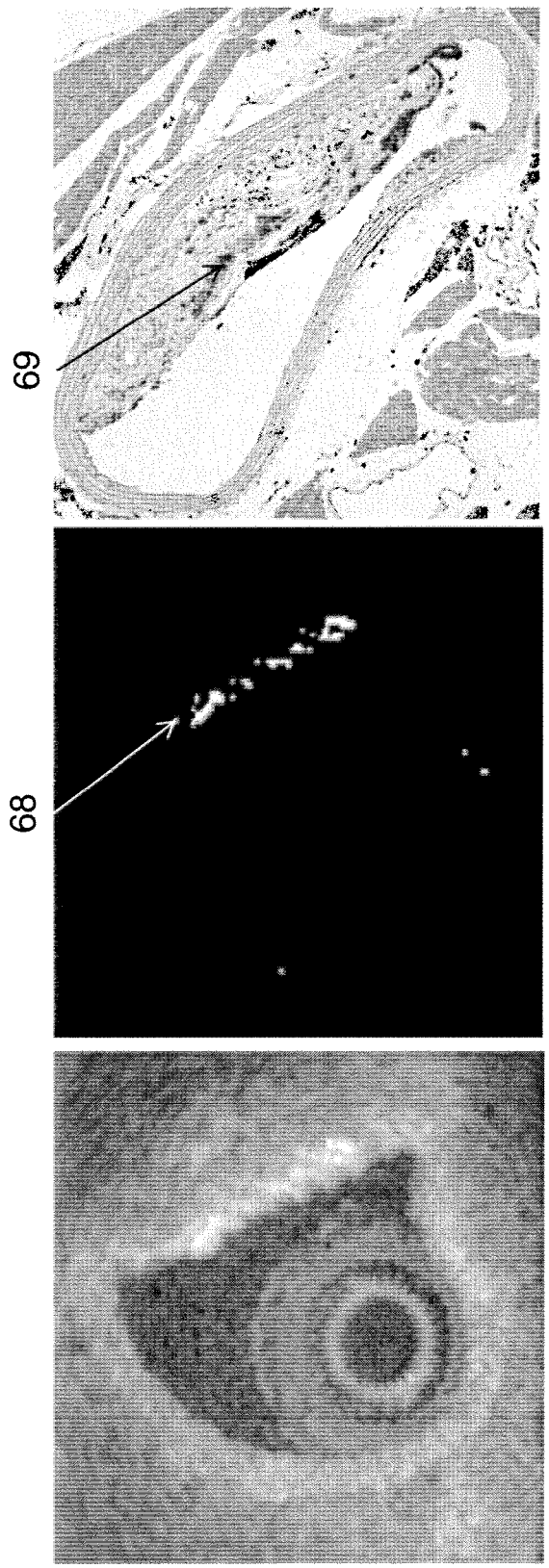
FIG. 16A-C illustrates an example original OCT of a blood vessel, resulting macrophage segmentation of the image in FIG. 16A, and the corresponding histology of the blood vessel.

For mice, macrophage segmentation is only performed to the pixels within the superficial aorta layer. In one implementation, the region of interest is chosen to be the superficial 100 μm layer in mice aorta. In step 64, the region of interest is automatically segmented by first segmenting the lumen and then searching the 100 μm thick layer (67) from the lumen. One example is shown in FIGS. 15A-C. FIG. 15A shows the original OCT image. FIG. 15B shows the segmented lumen 66. FIG. 15C shows the 100 μm thick layer 67 from the lumen 66 segmented as shown in FIG. 15B. Pixels within the layer 67 are classified using the decision trees and only macrophages are kept. FIG. 16A-C illustrates the segmentation results and the corresponding histology. FIG. 15A shows an original OCT image, while FIG. 16B shows corresponding macrophage segmentation results 68. FIG. 16C illustrates the histology corresponding to the vessels shown in FIGS. 16A and 16B.

Figure 17:
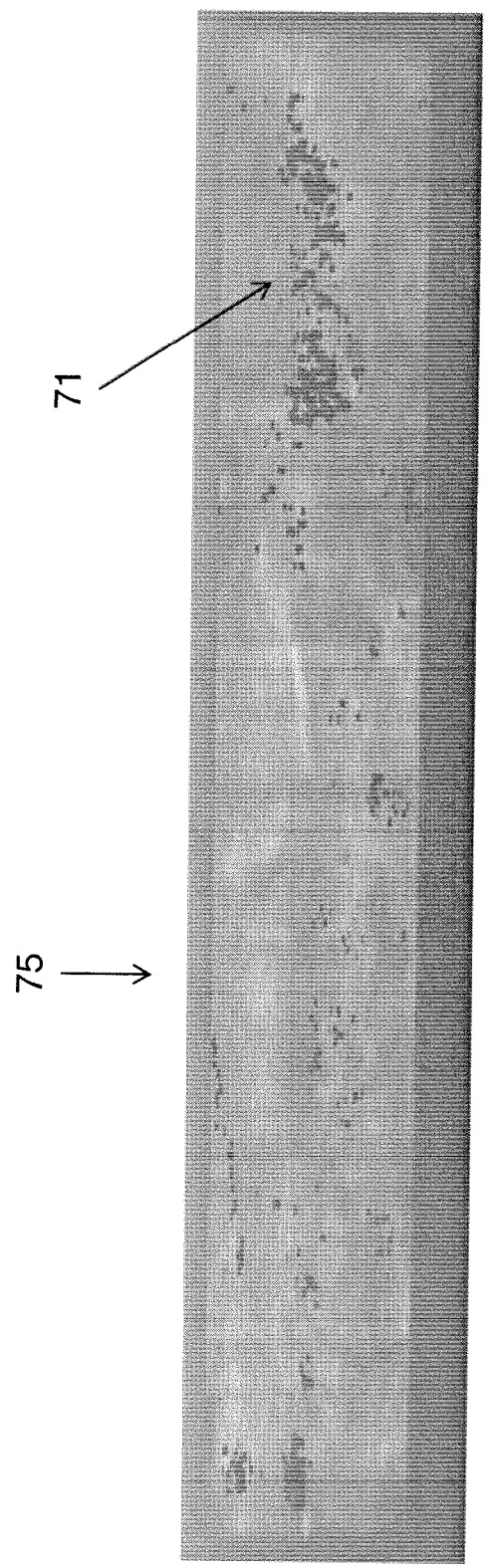
FIG. 17 illustrates a virtual mapping of macrophages in a virtually opened aorta.

Macrophage quantification 39 can be realized in different ways. In one embodiment, the area of the macrophage can be calculated and the results may be reported by average area/cross section, or total area/pull back. In another embodiment, the entire aorta can be virtually opened and extended flat. The segmented macrophage can be mapped to the surface of the opened aorta by maximum intensity projection. The macrophage area can be reported by the percentage of the entire aorta surface. FIG. 17 illustrates the latter virtual opening visualization of the aorta 75. Segmented macrophages 71 may be colored red in order to mimic mac-3 staining in histology. While the system and methods described above in connection with macrophage segmentation step 38 and quantification step 39 are made with reference to 2D input data, 3D input data may also be used.

Plaque Characterization

Characterization of fibrous and lipid plaques may be performed based on vessel wall segmentation results. In one embodiment, training features including but not limited to: intensity, attenuation coefficient, edge sharpness (described by the slope of the intensity profile across the edge), presence of media, presence of adventitia, texture information such as statistics from Gray-Level Co-Occurrence Matrix (GLCM), Gabor filtered images and different frequency information from wavelet filtered images or decomposed from wavelet packets, can be used to build decision trees, which are further used to classify the atherosclerotic plaques within the vessel wall 46 or 47 shown in FIGS. 8, 9A and 9B. Based on the classification results, plaques can be displayed in different colors indicating their types.

Adjacent line and adjacent frame information are also utilized for tissue classification. In one embodiment, based on single A line classification results, the final tissue type of one A line is determined by the majority of tissue types in adjacent lines and adjacent frames. The continuousness of tissue in both 2D frame and 3D volume is also taken into account in tissue classification.

Fibrous Cap Segmentation and Quantification

With reference to FIG. 3, the fibrous cap (FC) segmentation step 40 is implemented before quantification of FC. FC is delineated by a luminal boundary and an abluminal boundary. The luminal boundary is the same as the vessel lumen contour and may be segmented using the DP algorithm discussed previously. The FC abluminal boundary has a high intensity difference between the FC and lipid pool, and a high optical attenuation. An energy function dependent on the combination of the intensity difference and attenuation to each pixel in the ROI may be assigned. In one embodiment, the energy function defined as follows is assigned to each pixel inside the ROI:

$$e\_FC(i,j) = \bar{I}(i-d_v \leq i_\alpha \leq i,j) - \bar{I}(i < i_\alpha \leq d_{max},j) - \lambda\mu_a$$

Where $d_v$ and $d_{max}$ are predefined depths to calculate optical intensity difference, $\mu_a$ is optical attenuation extracted from the A line segment of length L across (i, j), and $\lambda$ is a weighting term. All these parameters can be determined experimentally using training images and expert manual tracing as references. The ROI containing FC can be determined semi-automatically or fully automatically. In one embodiment, the starting and ending angle of FC are given by the users to determine ROI, which is automatically extracted as the region between the segmented lumen boundary and a predefined maximum depth. In another embodiment, the ROI can be determined from the plaque characterization step 85.

With fully segmented FC, we can quantify not only the minimum FC thickness, but also FC thickness at every point on the boundary, and volumetric metrics including surface area and volume. The thickness at each point of FC luminal boundary is defined as the minimum distance from this point to the FC abluminal boundary. The conventional minimum FC thickness of a single lesion can be simply found as the minimum thickness of all the points on the FC luminal boundary in all the consecutive frames covering the lesion. This definition provides that, given a segmented FC, the FC thickness is consistent and independent of catheter position, FC angular position and lumen shape.

The surface area of FC can be calculated as the product of the frame interval and the arc length of FC. The arc length can be determined from the radius of FC luminal boundary with reference to the centroid of the lumen. The surface area in a thickness category can be also calculated. For example, FC may be divided into 3 categories: <65 µm, 65-150 µm and >150 µm. The categories are based on both pathology studies and in vivo clinical studies using IVOCT (Image Visualization OCT). Other cut-off values of thickness may be used. FC volume is calculated from cross sectional FC areas in individual frames using Simpson's rule. FC volume density is the FC volume normalized by the lesion length. Cross correlation between the volumetric metrics can be used to evaluate redundancy.

Stent Detection

With reference to FIG. 3, the stent detection step 82 is applicable to different types of stents, including but not limited to, bare-metal stents (BMS), drug-eluting stents (DES) and bioasorbable everolimus-eluting stent system (BVS). Once the detection of stents is performed, an analysis of the stent's structure and coverage within a vessel may be performed, as shown in step 83 in FIG. 3.

Detection of Metallic Stents

Figure 19:
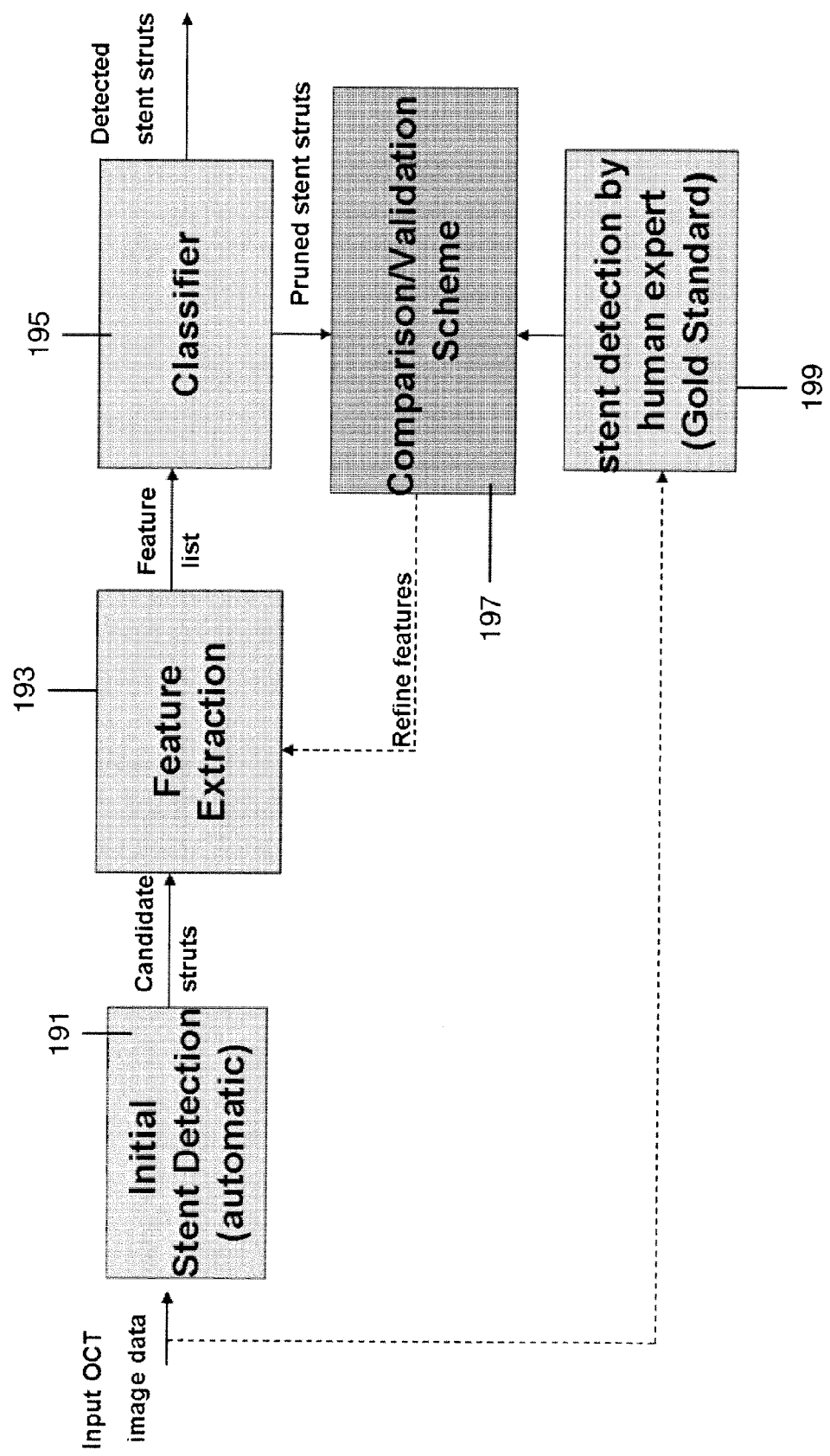
FIG. 19 illustrates steps comprising an example metallic stent segmentation.

Steps comprising an example metallic stent segmentation are illustrated in FIG. 19. An automatic initial stent detection (screening) is performed on the input OCT image through image processing techniques. Steps include (i) image preprocessing to remove guidewire shadow, (ii) lumen detection by dynamic programming, (iii) shadow detection by morphological processing and linear feature detection using the Hough transform, and (iv) locating the maximum valued pixel (in terms of intensity) in a small search region set using shadow detection process of step (iii).

Figure 20B:
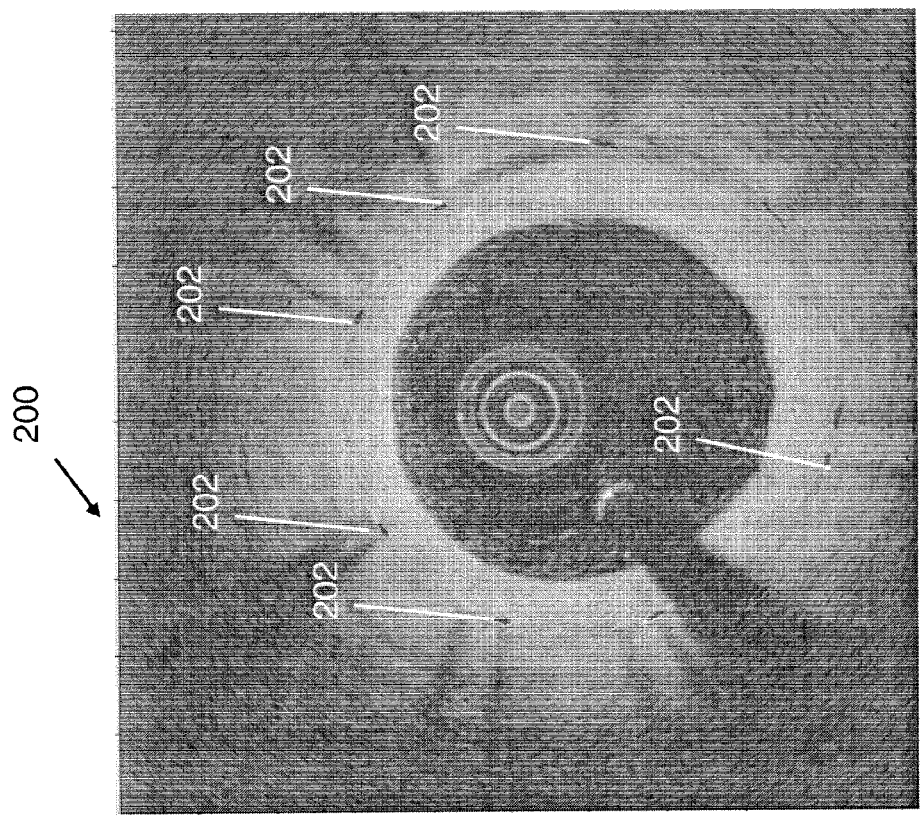
FIGS. 20A and 20B illustrate cross-section images without stent detection results and with stent detection results overlayed, respectively.
Figure 20A:
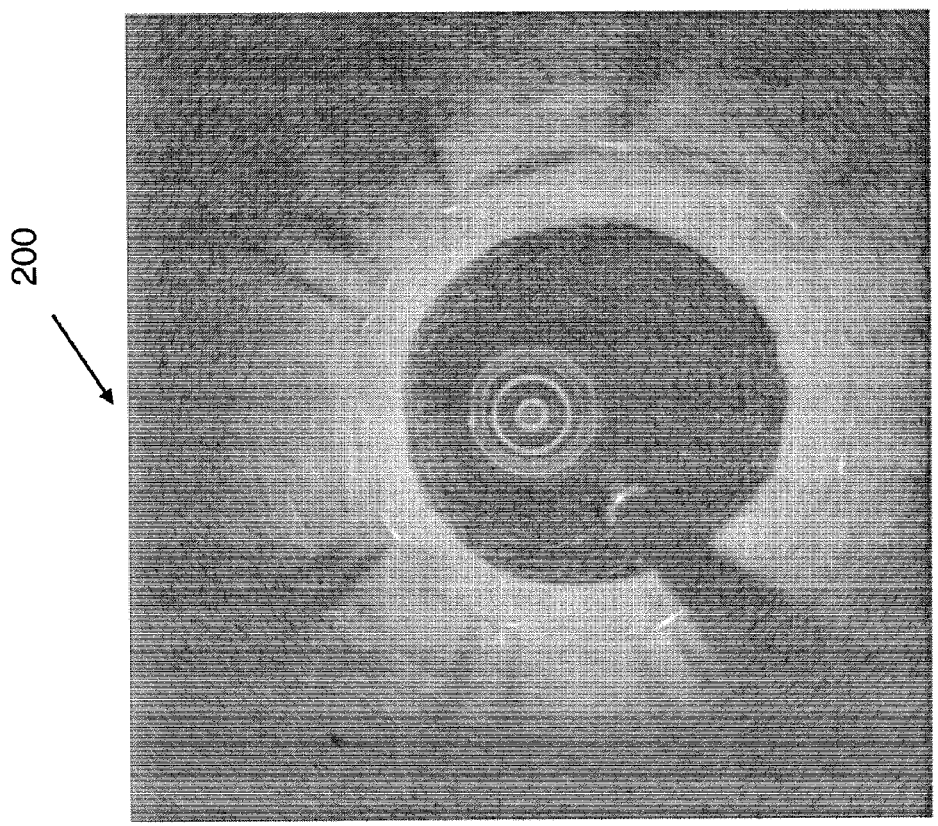

Features from the screened candidate stent struts are extracted and used in a supervised classifier to "prune" stent struts. An optimal feature list to use in the classifier is computed by employing a feedback process that evaluates classifier performance with each possible subset of features from the feature list. FIGS. 20A and 20B illustrate cross-section images 200 without stent detection results, and with stent detection results 202 overlayed, respectively. For evaluations and comparisons, ground truth (gold standard) data provided by a panel of human experts in interventional cardiology may be employed. Such experts can manually segmented stent struts from many OCT pullback sequences.

The stent detection technique can also be generalized to 3D. In one embodiment, search tolerances for stent struts in CS pullback image i+1 are set based on detected stent struts in pullback image i. Other 3D methods for stent detection may be implemented such as those that involve building mathematical model of the stent in 3D. For example, a CT scan of the stent could be employed to derive the aforementioned model, which would then assist in predicting possible stent strut locations in 3D.

Detection of Bioresorbable Everolimus-Eluting Stent System (BVS)

Different than BMS, BVS stents exhibit as protruding boxes 210 in the lumen of arteries in the baseline cases as shown in FIGS. 21A-C. For the follow-up cases, the BVS stents can present as "black boxes" or other appearances. For BVS stents in baseline cases, the stent detection also involves initial segmentation of lumen (step 32). Based on the lumen boundary, two approaches may be used to detect the stent boundary. With reference to FIG. 21B, in one embodiment, the Hough transform can be used to detect the BVS stent lateral boundary in the rectangular view, represented as quasi-straight lines protruding into the lumen. Then, the detected lines are clustered into individual stents 210 based on their mutual spatial interval and presence of stent material between adjacent boundaries. In another embodiment, a deformable template matching method, such as described in A. K. Jain, Z. Yu and S. Lakshmanan, "Object matching using deformable templates," Pattern Analysis and Machine Intelligence, IEEE Transactions on 18(3), 267-278 (1996), incorporated herein by reference can be used to directly detect the protruding boxes in the anatomical view OCT images. Prior knowledge of the shape of the stent can be used to build a template, which can be deformed into different shapes by using a set of parameters. An energy function is associated with the model to tolerate the deviation of the template and its matching with the original images and a probability distribution is defined to bias the choice of possible templates. For follow-up cases, the same deformable template matching approach can be used to detect the "black boxes" within the arterial layer.

In yet another embodiment, the BVS stent detection can be performed using a classification method. Features including but not limited to the following may be considered: (1) The shape of the BVS strut, represented as a rectangular frame in OCT images. The shape can appear as deformed rectangles due to the eccentricity of imaging wire or different designs of stent types. A training database may be used to build a template library including all possible shapes for BVS struts. Templates are sorted according to the probability density function drawn from the statistics of the training library and use the sorted templates for future stent detection. (2) The relative intensity difference between the stent boundary, where there is high reflection/backscattering, and stent core, where little light is backscattered due to the uniform materials making up the struts. (3) Relative positions of strut with respect to adjacent struts and lumen boundary. An initial screening may be performed to detect candidate struts, based on which a spline contour may be fitted. The potential under-called and over-called struts may be classified using the information of the relative distance between the struts and the fitted spline contour. In addition, a priori information can be used such as the strut-lumen relative location. In baseline cases, well deployed struts are disposed on the lumen boundary, and malaposed struts may be inside the lumen. In follow-up cases, struts will likely be covered by neointima. (4) 3D model for specific stent types. The 3D model provided by the manufacturer can be used to predict individual strut locations in cross sectional frames to further increase the robustness of the methods described herein.

3D Stent Model

Figure 24:
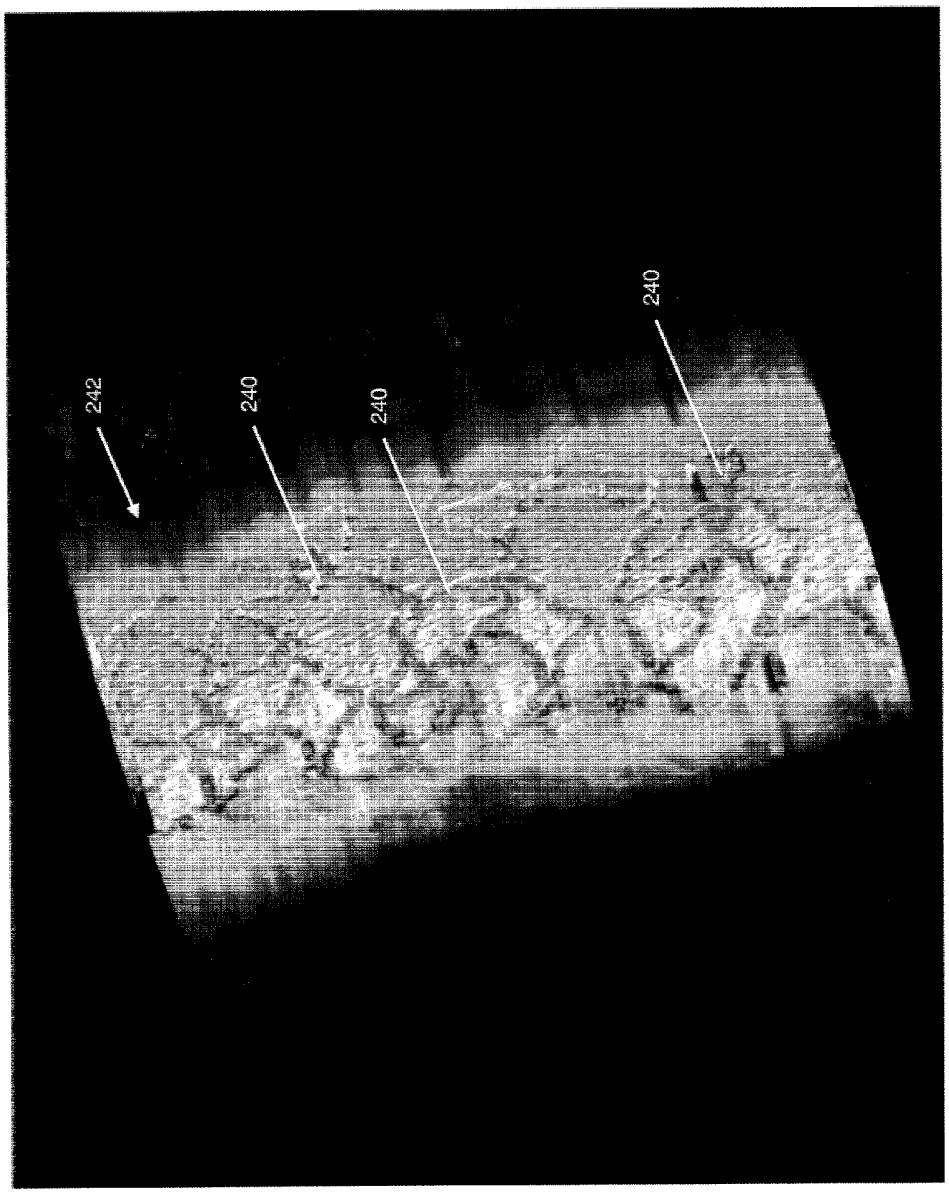
FIG. 24 illustrates 3D rendered metallic stents overlying on the vessel.

A stent is a tubular structure made up of wires or polymer supports in a regular structure (FIGS. 24, 25A and 25B). A priori 3D knowledge of stent structure may be used to enhance strut detection. One approach that may be utilized adds features corresponding to patterns present in the stent with a local structural model (LSM) of the repeating structural unit in a stent. This utilizes the stent wire structure locally. The LSM model can be used for both metallic stents and BVS stents detection.

Stents are typically made up of repeating smallest-units. For example, FIG. 24 illustrates a 3D image showing rendered metallic stents having repeating diamond shaped patterns overlying on the vessel 242, while FIGS. 25A and 25B illustrate a 3D view and fly-through view, respectively, of BVS stents 250 also having a regular repeating geometric pattern inside a vessel 252. Other stent designs have similarly repeating units, albeit with different structures. An LSM may be constructed consisting of a "stick" model representing the stent wires, with appropriate angles between them. The LSM may use the smallest-unit, plus adjoining units, creating a stick-figure surface patch to apply to image data. At each candidate strut, the LSM is fit to nearby accepted-struts using a distance objective function. A candidate strut can be made up of any point on the smallest-unit. The smallest unit is divided into evenly spaced points, for example 25 points, and each point is tested. For each point, the LSM is fit to accepted-struts with 3 free parameters corresponding to the 3 possible angulations of the LSM. Potential constraints for optimization would restrict angulations of the LSM so that it is nearly parallel to the lumen surface. The best fit over all test points gives the minimum average distance between accepted struts and the locally best fit LSM. This distance should be relatively low if the candidate strut is indeed a strut, thereby providing a powerful 3D feature for stent detection. There are many potential variations to this algorithm. In one possible variation, optimization for each test point can be done in a non-iterative fashion with appropriate mathematical description of the stick figure, thereby greatly speeding implementation. The LSM may also have stretching parameters. For example, the LSM may be fitted by a spline and deformed by moving the anchor points on the splines. Alternatively, the deformation can be done using Fourier domain methods by constructing an orthogonal cosine series as the foundation for deformation. In addition, construction of a full 3D model of an entire wire stent may be performed.

Stent Quantification

Several quantitative measures can be derived from the detected/segmented stents with reference to the segmented lumen, including but not limited to, number of uncovered and covered stent struts, number of malaposed stent struts 214, stent area, area of coverage computed as (stent area-lumen area) applicable to follow-up cases, coverage thickness for each strut and coverage thickness versus angle. For BVS stents, after the struts are detected, the stent scaffold 212, which is the outer boundary of the stent, can be automatically generated using a spline interpolation algorithm, the results of which are shown in FIG. 21C. The area of the scaffold can be used to characterize how well the stent is expanded inside the vessel. Malaposed struts 214 can be automatically classified based on whether the struts are attached to the lumen boundary. Other clinically relevant metrics, including the number of malaposed struts, scaffold area, strut area and effective blood flow area are recorded. For follow-up cases, the number of covered/uncovered struts may also be reported. Characterization of neointima (arterial intima formed on the stents) can be performed in a similar manner as in step 85.

Visualization

There are a variety of visualization methods to convey results of the disclosed image analysis methods. A goal is to provide information useful for live-time decisions/planning of clinical treatments, for analysis of previous clinical treatments (stents, drugs, genes, etc.), for similar purposes in preclinical studies, etc. Visualization can be done in 2D or 3D.

Figure 18B:
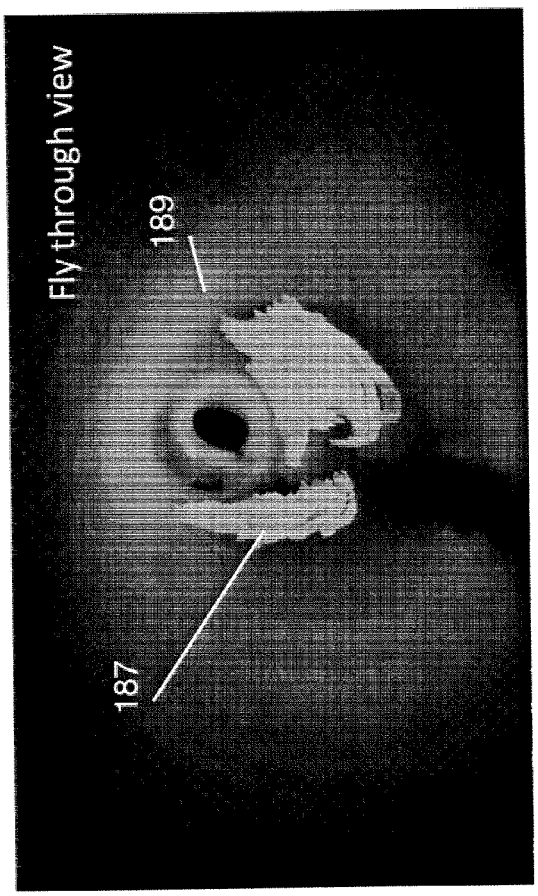
FIG. 18 illustrates different types of plaques present in a vessel indicated by different shading.
Figure 18A:
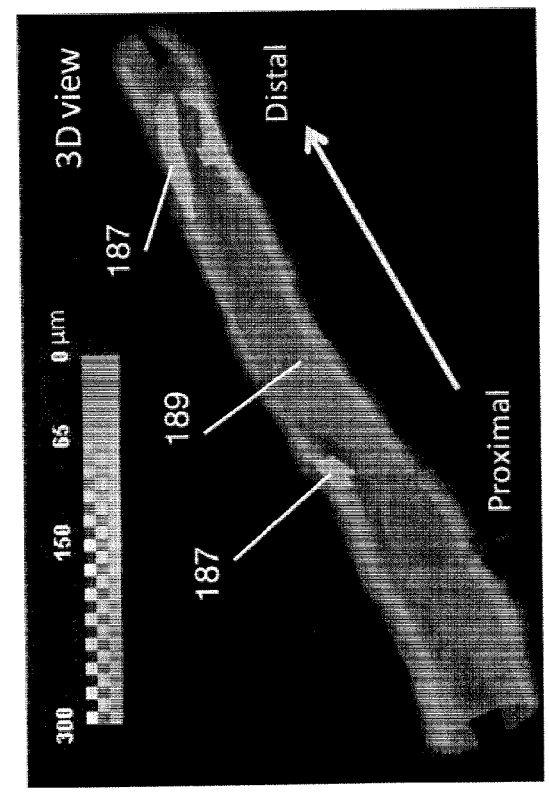

Automated segmentation results may be displayed in cross-sectional view (FIG. 4, FIG. 12, FIG. 16 and FIG. 20) or longitudinal view (FIG. 6 and FIG. 9) or enface view (FIG. 17). In addition, FIGS. 18A and 18B illustrate a 3D view, and fly through view, respectively of a blood vessel 189 having different types of plaques 187 indicated by different shading relative to one another and the blood vessel 189. Such representations may also show as differing colors.

Quantification results may be displayed in cross-sectional view or longitudinal view (FIGS. 6A and 6B), or reported in tables or text.

Surface and volume visualization techniques can also be used to give the viewer a quick view of the relative concentrations of macrophages, calcifications, etc., the smoothness or roughness of the lumen, extent of calcifications, etc. Such 3D image data can be viewed from any angle and virtually lighted from any angle in an interactive fashion. Another way to interact with such volumes is to digitally "slice" them along any plane or arbitrary surface to create a reformatted 2D view.

Figure 22:
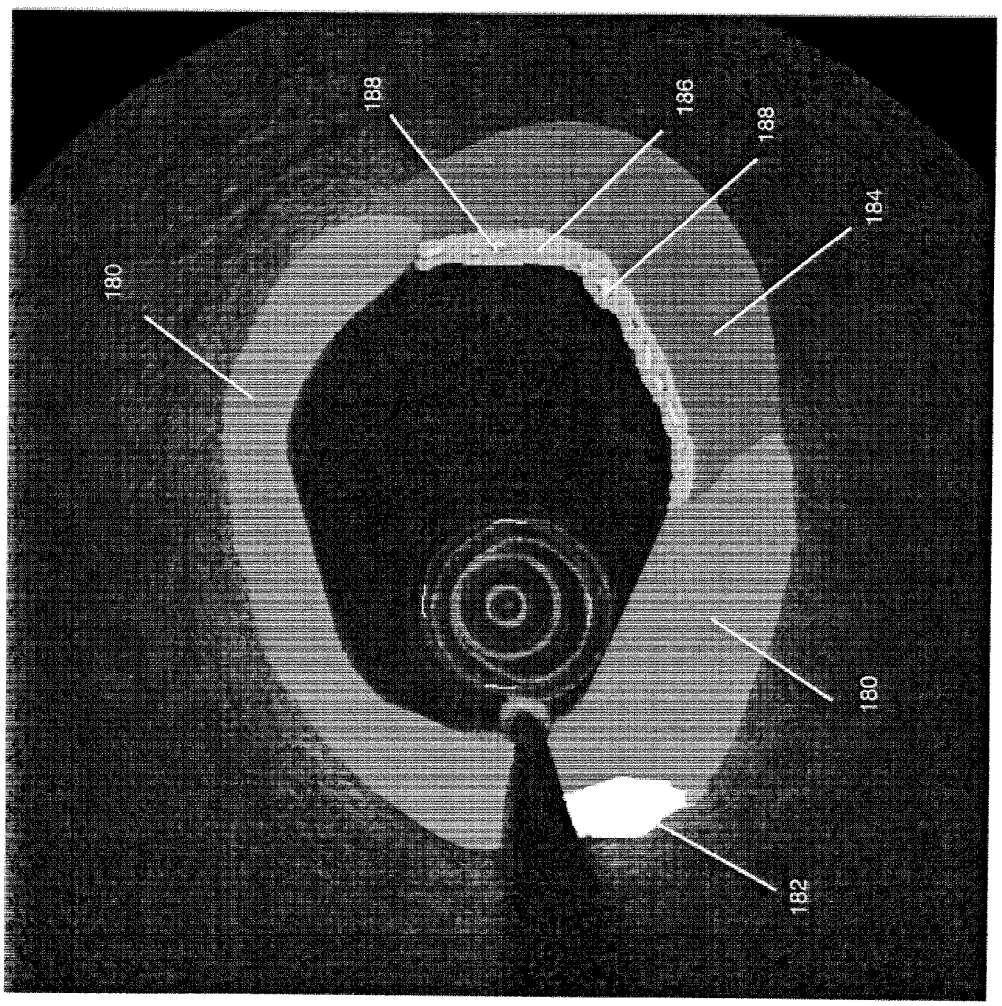
FIG. 22 illustrates automatically segmented intravascular OCT features.

After segmentation of the features in the arterial wall (steps 32, 36, 38, 40 and 82) and plaque characterization step 85, different types of plaques may be shaded or color-coded for visualization. As one example, a virtual histology OCT image is shown in FIG. 22. Fibrous 180, calcified 182 and lipid plaques 184 are shaded differently, but in another embodiment may be shown with different colors. Fibroatheroma 186 and macrophages 188 are also represented with different shading, which assists in visualization. Following plaque characterization, results can be presented to the viewer in such a way as to mimic observations that might be made in histology.

Figure 23:
FIG. 23 illustrates a calcified plaque and a lipid plaque rendered in 3D.

Automated segmentation results may also be displayed in 3D view. FIG. 23 illustrates a 3D rendered vessel with a segmented calcified plaque 190 shaded differently than the background shading of the vessel wall, and a lipid plaque 192 that is also shaded. A side branch 194 is also seen in the image.

A similar 3D view can be used in stent visualization as illustrated in FIG. 24. In one embodiment, detected metallic stents are rendered in red on the segmented vessel wall, rendered in white. In another embodiment, detected BVS stents may also be rendered in different shading or colors to differentiate from the vessel wall, as shown in FIGS. 25A and 25B.

Although all the segmentation techniques discussed herein are based on 2D or 2D+time images or image set, the methods can also be extended to 3D images. For example, the active contour model used in steps 35 and 36 may be directly implemented in 3D images with all the energy functions defined in 3D space.

The segmentation, quantification and visualization techniques described herein may be used for a variety of tasks, including without limitation atherosclerosis research, surgical planning, and determination of appropriate placement of stents. Further, the systems and methods described herein may be useful for computer-aided diagnosis of patients based on, for example, the likelihood of disease based on the quantification of calcified plaques, macrophages, fibrous tissue and thin fibrous caps.

OCT Image Visualization and Analysis Toolkit (OCTivat)

OCTivat is a toolkit for analyzing and visualizing IVOCT images for IVOCT researchers, interventional cardiologists, IVOCT Core Lab image analysts and image processing community. OCTivat is preferably developed in C++ using open source libraries, including Qt, Insight Segmentation and Registration Toolkit (ITK), and Visualization Toolkit (VTK). Because these libraries are cross-platform libraries, OCTivat is fully compatible with all major operating systems, including Windows, Macintosh and UNIX/Linux that may be implemented, for example, on imaging station 12 or workstation 14. Functions of OCTivat are analysis and visualization. Use of OCTivat is not limited to a particular IVOTC system, but rather may be implemented generally on any IVOCT system. OCTivat provides for IVOCT data post-processing. OCTivat is also easily extensible to include more features used for analysis and visualization. OCTivat may also include additional image analysis and visualization algorithms, such as those validated for clinical use.

Analysis Module of OCTivat

Figure 26:
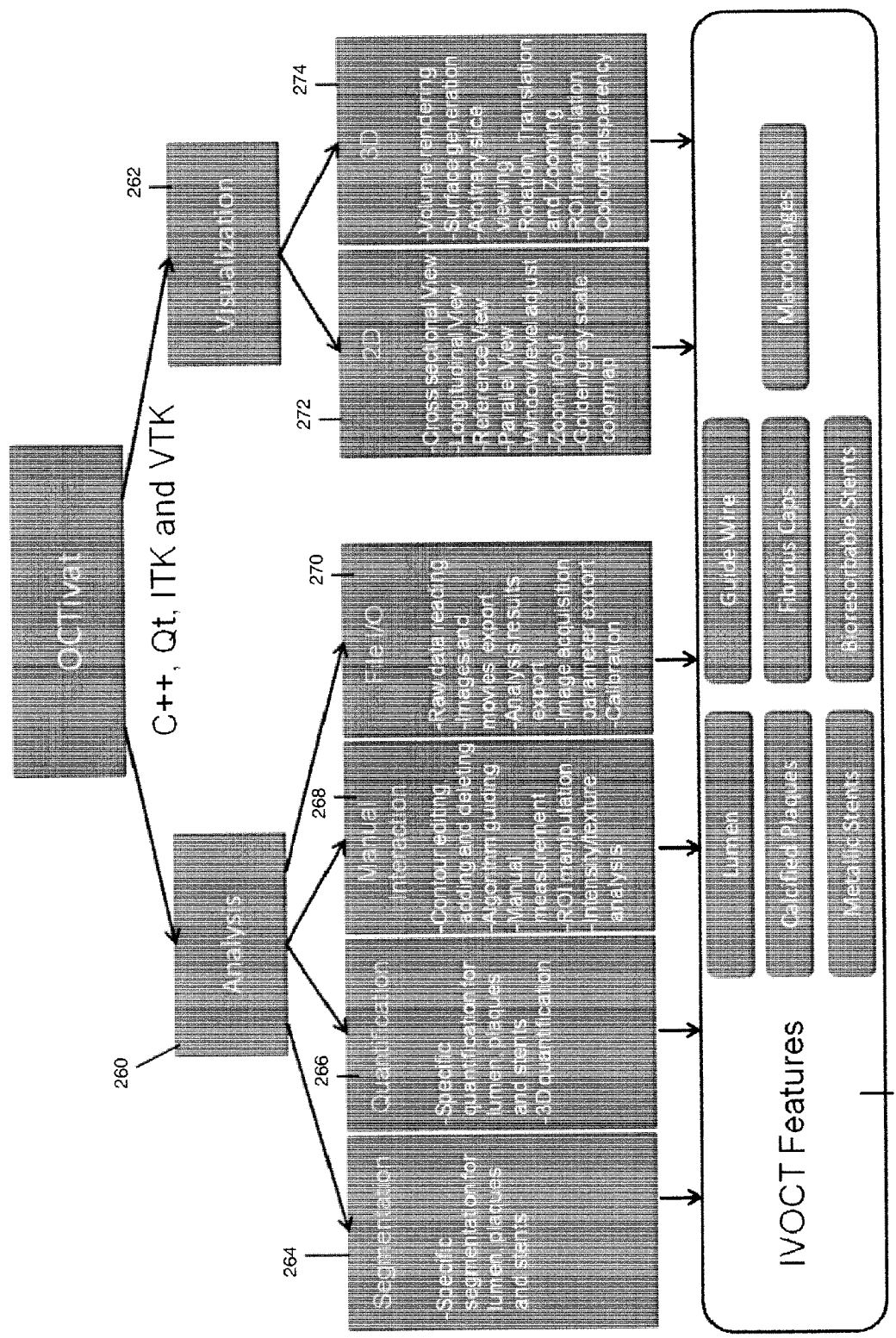
FIG. 26 illustrates aspects of the OCT image visualization and analysis toolkit (OCTivat).

FIG. 26 illustrates components and features 276 of IVOCT. The IVOCT has an analysis module 260, and visualization module 262. The analysis module 260 is further divided into segmentation 264, quantification 266, file I/O 270 and manual interaction modules 268. These four modules may be applied to all the IVOCT features (plaques, stents, etc.). Segmentation 264 involves either fully automated or semi-automated contour delineation of IVOCT feature boundaries. For fully automated methods, automated detection is incorporated. Quantification 266 is performed based on segmentation 264 results and is specific to different IVOCT features. File I/O 270 includes opening raw IVOCT data and associated image acquisition parameters, and saving all the image data and analysis results into file structures convenient for further analysis or reporting. File I/O 270 also includes calibration, such as Z-offset calibration and vessel diameter calibration. Manual interaction 268 allows users to correct, add and delete contours, guide algorithms in semi-automated methods, and manually measure some IVOCT features. It also allows users to select a Region of Interest (ROI) and check the intensity and texture information inside the ROI for tissue characterization. The IVOCT features may include one or all of the lumen, calcified plaques, fibrous caps, macrophages and metallic and bioresolvable stents and may further be extended to neointimal hyperplasia, thrombosis, microvessels, vessel resistance ratio, for example, under the OCTivat framework.

Visualization Module of OCTivat

Figure 27:
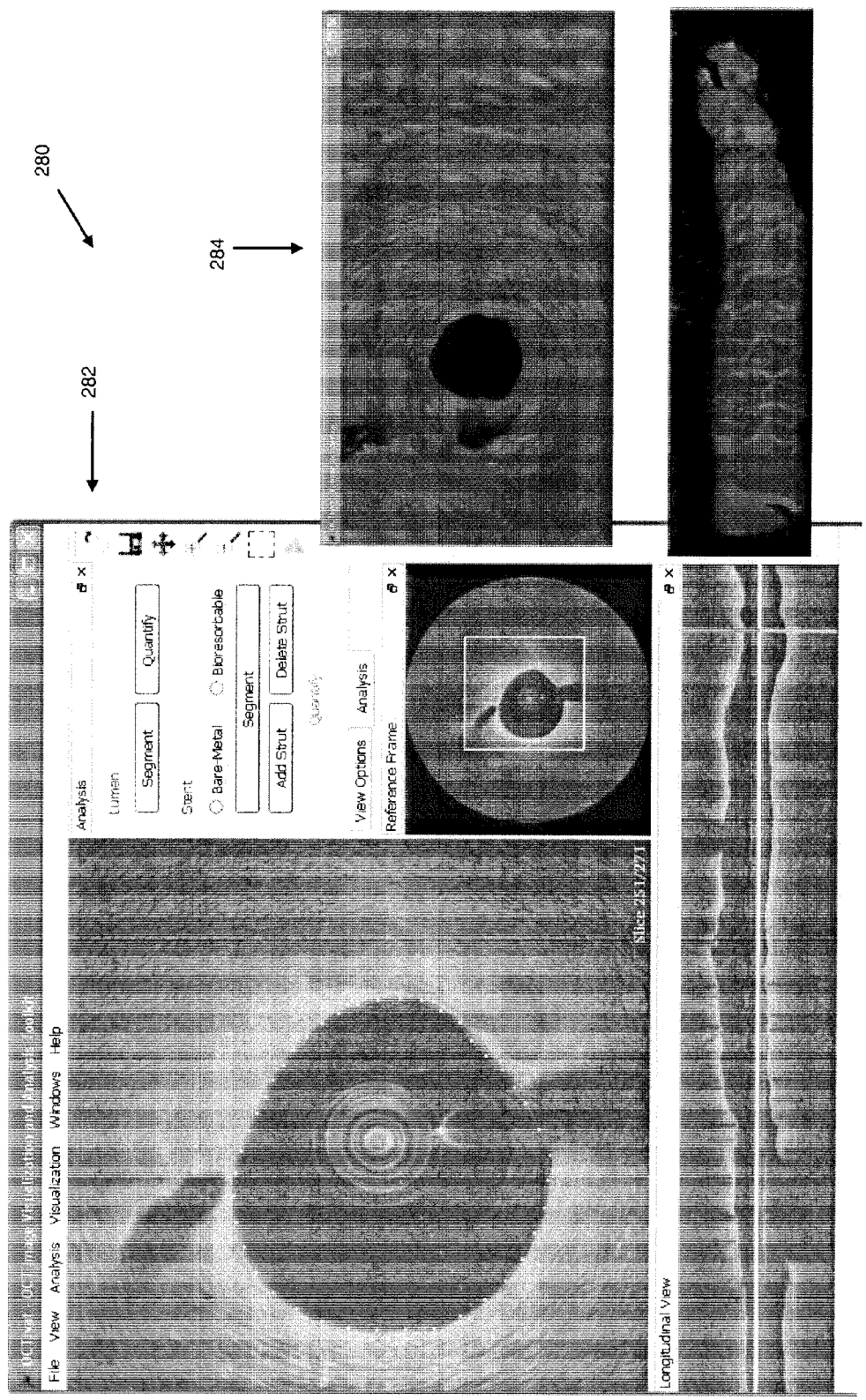
FIG. 27 illustrates the Graphical User Interface (GUI) of OCTivat.

An example of the Graphical User Interface (GUI) 280 associated with an exemplary IVOCT system according to the present disclosure is shown in FIG. 27. Both 2D and 3D visualization methods may be implemented. A 2D visualization 282 includes conventional cross section view and longitudinal view of IVOCT images. In addition, a parallel view enabling users to visualize adjacent 3-5 frames simultaneously can be provided. This is particular useful when the current frame information is obscured due to low SNR or artifacts. A 3D visualization 284 includes volume rendering and surface generation for all the IVOCT features. Users may toggle on and off specific features for desired visualization. Additional aspects that may be implemented include arbitrary slice viewing, and 3D ROI manipulation, enabling users to for example select, cut and manipulate certain segments of a vessel. Color and transparency panels for optimum visualization can also be provided.

The invention claimed is:

1. Computer-implemented segmentation and quantification method using an intravascular optical coherence tomography (OCT) system having an OCT signal emitting and receiving instrument comprising:
   obtaining an OCT image set comprising one or more images of a portion of a blood vessel;
   segmenting a lumen portion of at least one of the one or more images;
   segmenting an OCT signal emitting and receiving instrument portion of the at least one of the one or more images;
   segmenting a vessel wall portion of the at least one of the one or more images;
     wherein the segmenting a vessel wall portion step comprises obtaining at least one texture mapping by processing at least one of the one or more images with at least one Gabor filter; and,
     determining a contour having maximum texture difference inside and outside the contour by applying active contour processing to the at least one texture mapping;
   obtaining an initial contour for the active contour processing from a boundary determined in the segmenting the lumen portion step; and
   segmenting a calcified plaque portion of the at least one of the one or more images.

2. The method of claim 1, wherein the segmenting the lumen portion step comprises:
   obtaining at least one binary image by applying Otsu's method to at least one of the one or more images.

3. The method of claim 2 wherein the segmenting the lumen portion step comprises:
   determining a first pixel corresponding to a border of the lumen in a light propagation direction corresponding to the OCT signal emitting and receiving instrument.

4. The method of claim 1 wherein the segmenting the lumen portion step comprises:
   obtaining at least one binary image by applying Otsu's method to at least one of the one or more images;
   determining a boundary from the at least one binary image giving a global maximum for an energy function defined at least in part by an intensity difference of pixels inside and outside the boundary.

5. The method of claim 1 wherein the segmenting the OCT signal emitting and receiving instrument portion step comprises:
   obtaining at least one binary image of a bright superficial layer of the blood vessel; and,
   determining a location of a gap in the bright superficial layer.

6. The method of claim 1 wherein the segmenting a calcified plaque portion step comprises:

obtaining a segmented vessel wall portion of at least one of the one or more images from the segmenting the vessel wall portion step; and detecting the edge of a calcified plaque within the segmented vessel wall portion in at least one of the one or more images.

7. The method of claim 6 further comprising:

determining at least one initial contour from the detecting the edge of a calcified plaque step;

inputting the at least one initial contour and at least one of the one or more images to an active contour model;

determining at least one boundary of a calcified plaque having a local maximum intensity difference between outside and inside the at least one boundary in at least one of the one or more images.

8. The method of claim 1 wherein the segmenting a calcified plaque portion step comprises:

obtaining at least one initial contour;

inputting the at least one initial contour and at least one of the one or more images to an active contour model;

determining at least one boundary of a calcified plaque having a local maximum intensity difference between outside and inside the at least one boundary in at least one of the one or more images.

9. Computer-implemented segmentation and quantification method using an intravascular optical coherence tomography (OCT) system having an OCT signal emitting and receiving instrument comprising:

obtaining an OCT image set comprising one or more images of a portion of a blood vessel;

segmenting a lumen portion of at least one of the one or more images;

segmenting an OCT signal emitting and receiving instrument portion of the at least one of the one or more images;

segmenting a vessel wall portion of the at least one of the one or more images;

wherein the segmenting a vessel wall portion step comprises obtaining at least one texture mapping by processing at least one of the one or more images with at least one Gabor filter; and, determining a contour having maximum texture difference inside and outside the contour by applying active contour processing to the at least one texture mapping;

obtaining an initial contour for the active contour processing from a boundary determined in the segmenting the lumen portion step; and, segmenting a macrophage portion of the at least one of the one or more images.

10. The method of claim 9, wherein the segmenting the lumen portion step comprises:

obtaining at least one binary image by applying Otsu's method to at least one of the one or more images.

11. The method of claim 10 wherein the segmenting the lumen portion step comprises:

determining a first pixel corresponding to a border of the lumen in a light propagation direction corresponding to the OCT signal emitting and receiving instrument.

12. The method of claim 9 wherein the segmenting the lumen portion step comprises:

obtaining at least one binary image by applying Otsu's method to at least one of the one or more images;

determining a boundary from the at least one binary image giving a global maximum for an energy function defined at least in part by an intensity difference of pixels inside and outside the boundary.

13. The method of claim 9 wherein the segmenting the OCT signal emitting and receiving instrument portion step comprises:

obtaining at least one binary image of a bright superficial layer of the blood vessel; and, determining a location of a gap in the bright superficial layer.

14. The method of claim 9 wherein the segmenting a macrophage portion step comprises:

classifying macrophages based on a decision tree dependent on manually segmented training images.

15. The method of claim 14 wherein the decision tree is dependent on one or more training features of the training images.

* * * * *